United States Patent
Unger

(10) Patent No.: US 9,737,727 B2
(45) Date of Patent: Aug. 22, 2017

(54) APPARATUSES AND METHODS FOR LASER LIGHT THERAPY OF HAIR

(71) Applicant: Martin G. Unger, Toronto (CA)

(72) Inventor: Martin G. Unger, Toronto (CA)

(73) Assignee: Martin G. Unger, Toronto (CA)

( * ) Notice: Subject to any disclaimer, the term of this patent is extended or adjusted under 35 U.S.C. 154(b) by 268 days.

(21) Appl. No.: 14/510,592

(22) Filed: Oct. 9, 2014

(65) Prior Publication Data

US 2015/0224339 A1     Aug. 13, 2015

Related U.S. Application Data

(60) Provisional application No. 61/937,276, filed on Feb. 7, 2014.

(51) Int. Cl.
*A61N 1/00*     (2006.01)
*A61N 5/06*     (2006.01)
*A61N 5/067*    (2006.01)

(52) U.S. Cl.
CPC ...... *A61N 5/0617* (2013.01); *A61N 2005/067* (2013.01); *A61N 2005/0629* (2013.01);
(Continued)

(58) Field of Classification Search
CPC .......... A61N 5/0617; A61N 2005/0644; A61N 2005/0629
(Continued)

(56) References Cited

U.S. PATENT DOCUMENTS

| | | |
|---|---|---|
| 2,397,757 A | 4/1946 | Schwedersky |
| 5,616,140 A | 4/1997 | Prescott |
| | (Continued) | |

FOREIGN PATENT DOCUMENTS

| | | |
|---|---|---|
| CN | 200976922 | 11/2007 |
| CN | 200977332 | 11/2007 |
| | (Continued) | |

OTHER PUBLICATIONS

D. Budd, D. Himmelberger, T. Rhodes, T.E. Cash, C.J. Girman, The effects of hair loss in European men: a survey in four countries, European Journal of Dermatology. vol. 10, No. 2, 122-7, Mar. 2000, Cas cliniques, http://www.jle.com/e-docs/00/01/89/92/article.phtml.

(Continued)

*Primary Examiner* — Amanda Patton
*Assistant Examiner* — Philip C Edwards
(74) *Attorney, Agent, or Firm* — Bereskin & Parr LLP/S.E.N.C.R.L., s.r.l.; Tony Orsi

(57) ABSTRACT

Various embodiments are described herein that generally relate to a low-level laser therapy (LLLT) device to aid in at least one of the prevention and treatment of hair loss, rejuvenation of hair, and stimulation of hair regrowth for a certain percentage of users. In at least one embodiment, a plurality of emitters and bristles may be arranged in rows on a concave active surface of a housing for facing a treatment surface of the user. In some embodiments, the device is a laser therapy helmet device, wherein a portion of the device rotates relative to the treatment surface during use. In at least some embodiments, the device may further comprise a plurality of modes of operation for delivering different amounts of energy to the treatment surface.

16 Claims, 18 Drawing Sheets

(52) U.S. Cl.
CPC ............... *A61N 2005/0644* (2013.01); *A61N 2005/0647* (2013.01)

(58) Field of Classification Search
USPC .......................................................... 607/79
See application file for complete search history.

(56) References Cited

U.S. PATENT DOCUMENTS

| | | |
|---|---|---|
| 6,497,719 B2 | 12/2002 | Pearl et al. |
| 6,666,878 B2 | 12/2003 | Carlgren |
| 7,194,316 B2 | 3/2007 | Bousfield et al. |
| 7,201,764 B2 | 4/2007 | Pearl et al. |
| 7,258,695 B2 | 8/2007 | Carullo, Jr. et al. |
| 7,331,964 B2 | 2/2008 | Maricle et al. |
| 7,597,708 B2 | 10/2009 | Carullo, Jr. et al. |
| 7,722,655 B2 | 5/2010 | Lee |
| 8,048,135 B2 | 11/2011 | Carullo, Jr. et al. |
| 8,083,696 B2 | 12/2011 | Vandenbelt et al. |
| 8,518,029 B2 | 8/2013 | Birmingham et al. |
| 8,574,276 B2 | 11/2013 | Gourgouliatos et al. |
| 2002/0188334 A1 | 12/2002 | Carlgren |
| 2003/0093915 A1 | 5/2003 | Pearl et al. |
| 2004/0147984 A1 | 7/2004 | Altshuler et al. |
| 2005/0251242 A1 | 11/2005 | Bousfield et al. |
| 2006/0084953 A1 | 4/2006 | Tankovich |
| 2006/0161226 A1 | 7/2006 | McMickle |
| 2006/0178712 A1 | 8/2006 | Carullo, Jr. et al. |
| 2007/0149900 A1 | 6/2007 | Lin |
| 2007/0256212 A1 | 11/2007 | Rabin |
| 2008/0125835 A1* | 5/2008 | Laurent ............... A61N 5/0617 607/89 |
| 2008/0172115 A1 | 7/2008 | Gourgouliatos et al. |
| 2008/0269732 A1 | 10/2008 | Pyun |
| 2009/0012586 A1 | 1/2009 | Kepecs |
| 2009/0024116 A1 | 1/2009 | Mulhauser et al. |
| 2009/0036954 A1 | 2/2009 | Ragazzi et al. |
| 2010/0004570 A1 | 1/2010 | Torres Martin |
| 2010/0106077 A1 | 4/2010 | Rabin et al. |
| 2011/0015707 A1 | 1/2011 | Tucker et al. |
| 2011/0138556 A1 | 6/2011 | Sanchez Martinez |
| 2012/0123305 A1* | 5/2012 | Pearl ................... A61N 5/0617 601/15 |
| 2012/0265274 A1 | 10/2012 | Gomez De Diego |
| 2013/0030506 A1 | 1/2013 | Bartolone et al. |

FOREIGN PATENT DOCUMENTS

| | | |
|---|---|---|
| CN | 101125233 | 2/2008 |
| CN | 202637742 | 1/2013 |
| CN | 103211377 | 7/2013 |
| EP | 0130950 B1 | 4/1990 |
| EP | 1257324 B1 | 1/2010 |
| EP | 2140911 A1 | 1/2010 |
| EP | 1988968 B1 | 9/2011 |
| JP | 2012075543 | 4/2012 |
| KR | 1020100132336 | 12/2010 |
| KR | 10-1169721 B1 | 7/2012 |
| KR | 10-1202822 B1 | 11/2012 |
| WO | 0160457 A1 | 8/2001 |
| WO | 2007101067 A2 | 11/2007 |

OTHER PUBLICATIONS

Norwood, O'Tart, Shiell, Richard C.: Hair Transplant Surgery, a text, Charles C Thomas Pub Ltd., Apr. 1984, pp. 4-5, 9-13.
Unger, Martin G., Low-Level Laser Therapy is Now a Do-It-Yourself Treatment, press release of the International Society of Hair Restoration Surgery, New York, Oct. 16, 2003. http://www.ishrs.org/press-release/low-level-laser-therapy-now-do-it-yourself-treatment.
Robert S. Haber and Dowling B. Stough, Flair Transplantation, Procedures in Cosmetic Dermatology, 2006, Elsevier Inc., ppl. 139-140, 149, 188-190.
Quan Q. Dinh, Rodney Sinclair, Female pattern hair loss: Current treatment concepts, Clin Interv Aging, Jun. 2, 2007 (2): 189-199, http://www.ncbi.nlm.nih.gov/pmc/articles/PMC2684510.
Oaze, Oaze Hair Beam Low Level Laser Therapy Message White Helmet: Hair Loss Prevention Hair Regrowth Deivce, printed from www.amazon.com/Oaze-Level-Therapy-Message-Helmet/dp/B0090U2SJS, printed Sep. 24, 2013.
LaserCap Company—Transdermal Cap, printed from http://lasercaprx.com/lasercap_canada_labeling.php.
Hair Loss Control Clinic, Ultimate 25 Laser, www.hlcconline.com/001LAHHUL25D.html printed Aug. 30, 2013.
Hair Loss Control Clinic, Ultimate II Laser, www.hlcconline.com/001LAHHUL02.html printed Aug. 30, 2013.
x5 Hair Laser, www.x5hairlaser.com printed Sep. 10, 2013.
Pekka J. Pontinen, Low Level Laser Therapy as a Medical Treatment Modality, Art Urpo Ltd., Biological effects of LLLT, pp. 99-100.
Lexington International, LLC Press Release, Hairmax Lasercomb Cleared for Prevention of Hair Loss and Stimulation of Hair Regrowth in Men and Women by Health Canada, www.hairmax.co.za/canadian_approval.htm, printed Sep. 25, 2013.
HairMax Laser Comb FDA Clearance, www.hairmax.com/fda-clearance printed Sep. 25, 2013.
James L. Breeling and Debbie Baratz, Low-Level Laser Therapy (LLLT) for Treatment of Androgenetic Alopecia in Men & Women, dated Oct. 22, 2009 http://hairfoundation.org/hair-library/artlicle-llt.htm.
Sunetics International, Breaking News: Sunetics gets FDA clearance (Jun. 2013) to Promote Hair Growth, www.sunetics.com, printed Aug. 26, Aug. 30 and Sep. 10, 2013.
Nutreve Hair Loss Prevention, Nutreve Personal Hair Therapy Laser, www.nutrevehairloss.com, printed Aug. 30, 2013.
HairMax, The science of hair growth. www.hairmax.com printed Sep. 10, 2013 and Oct. 21, 2013.
Igrow Hair Rejuvenation System, Laser hair loss treatment. www.igrowlaser.ca printed Oct. 21, 2013.

* cited by examiner

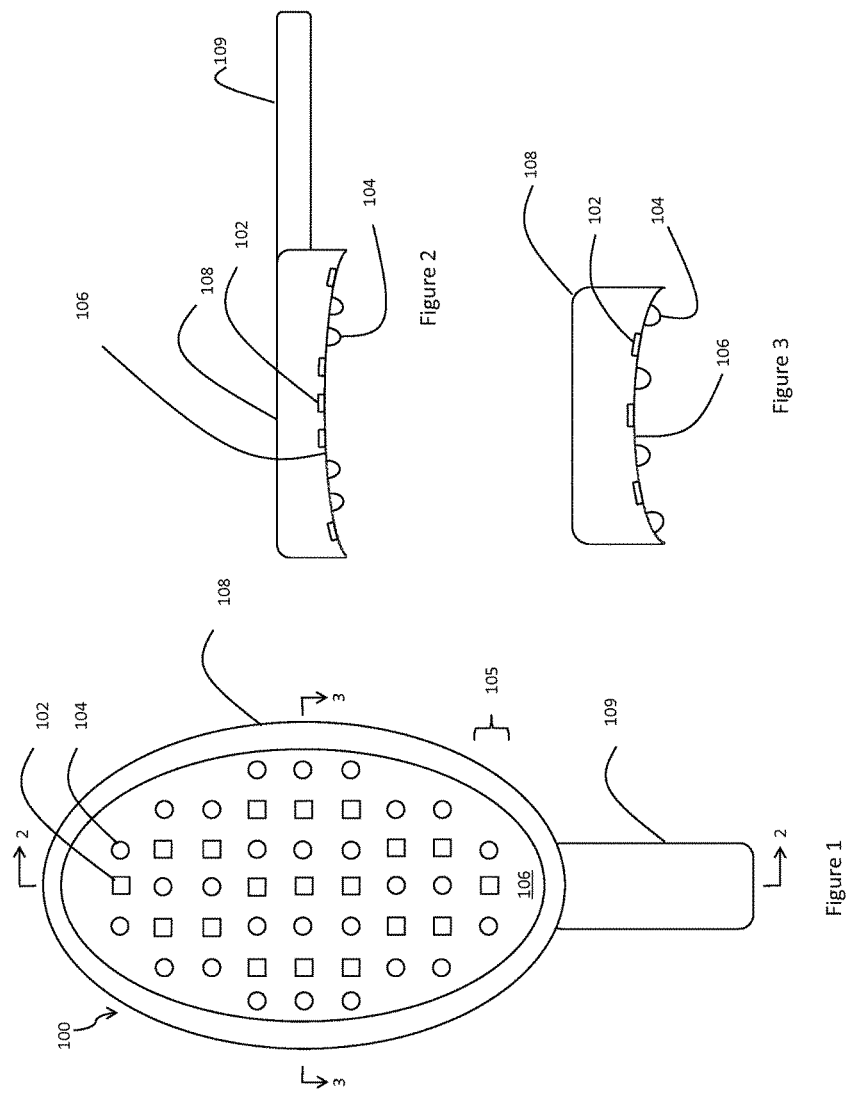

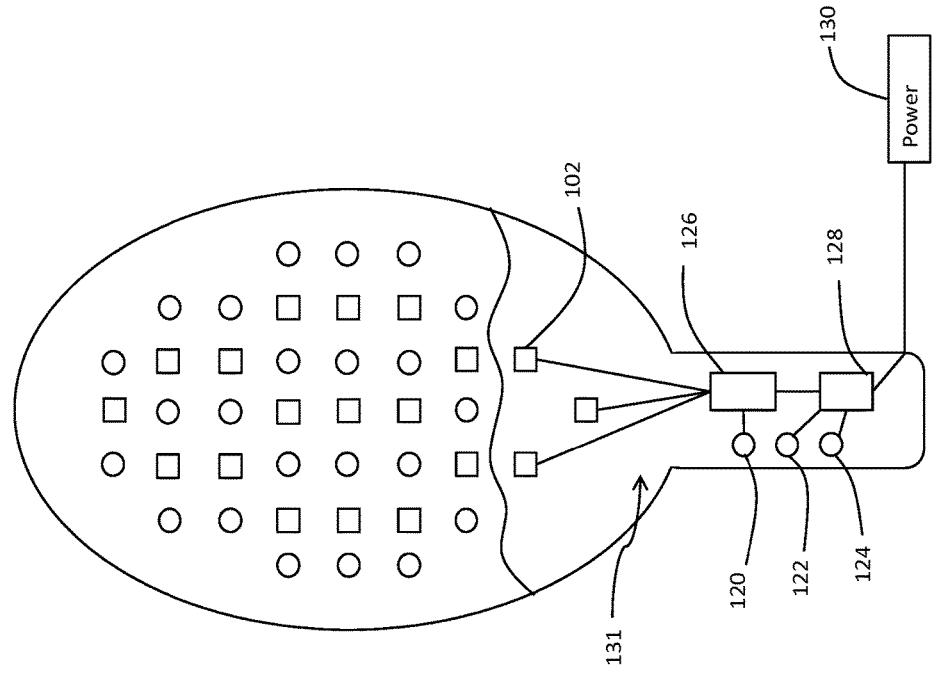
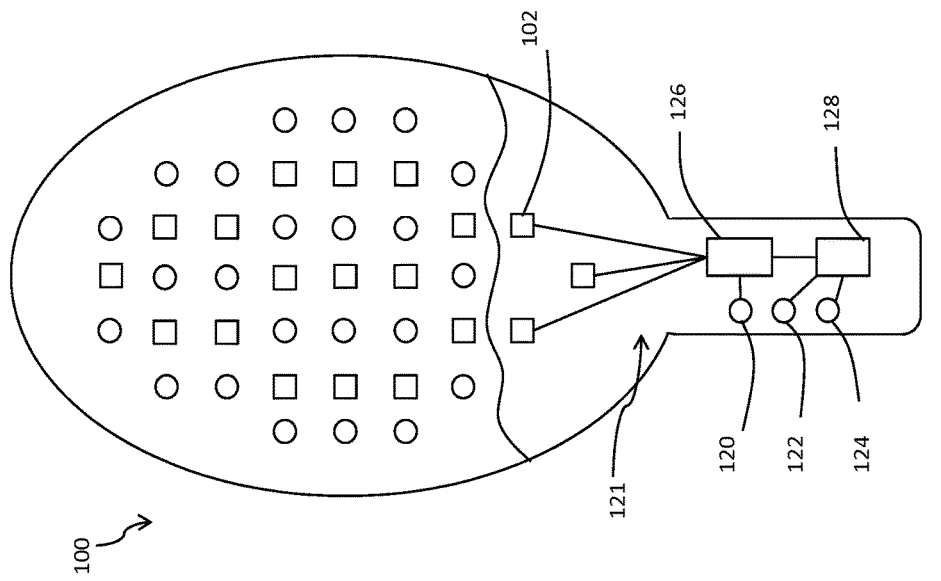

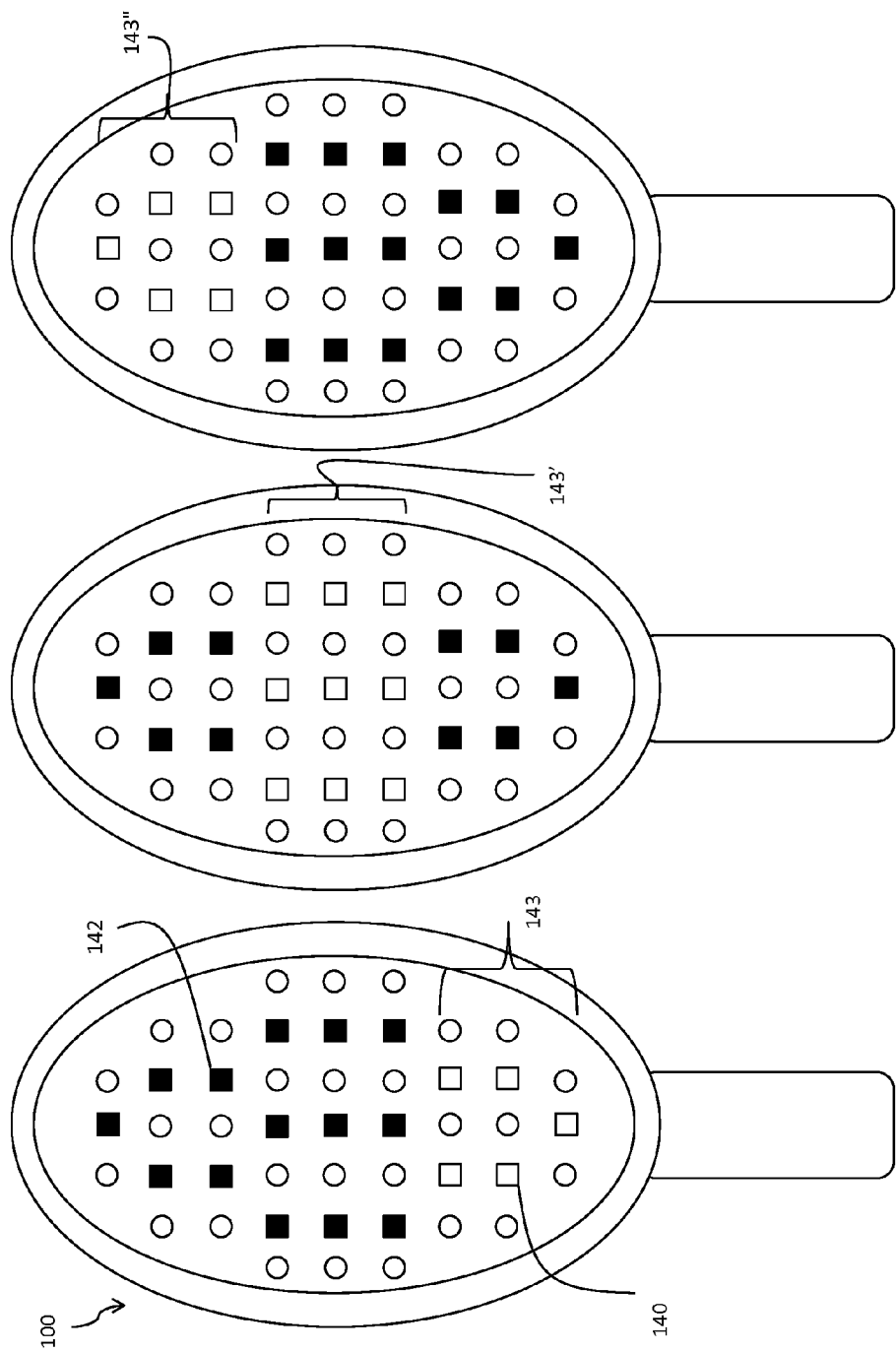

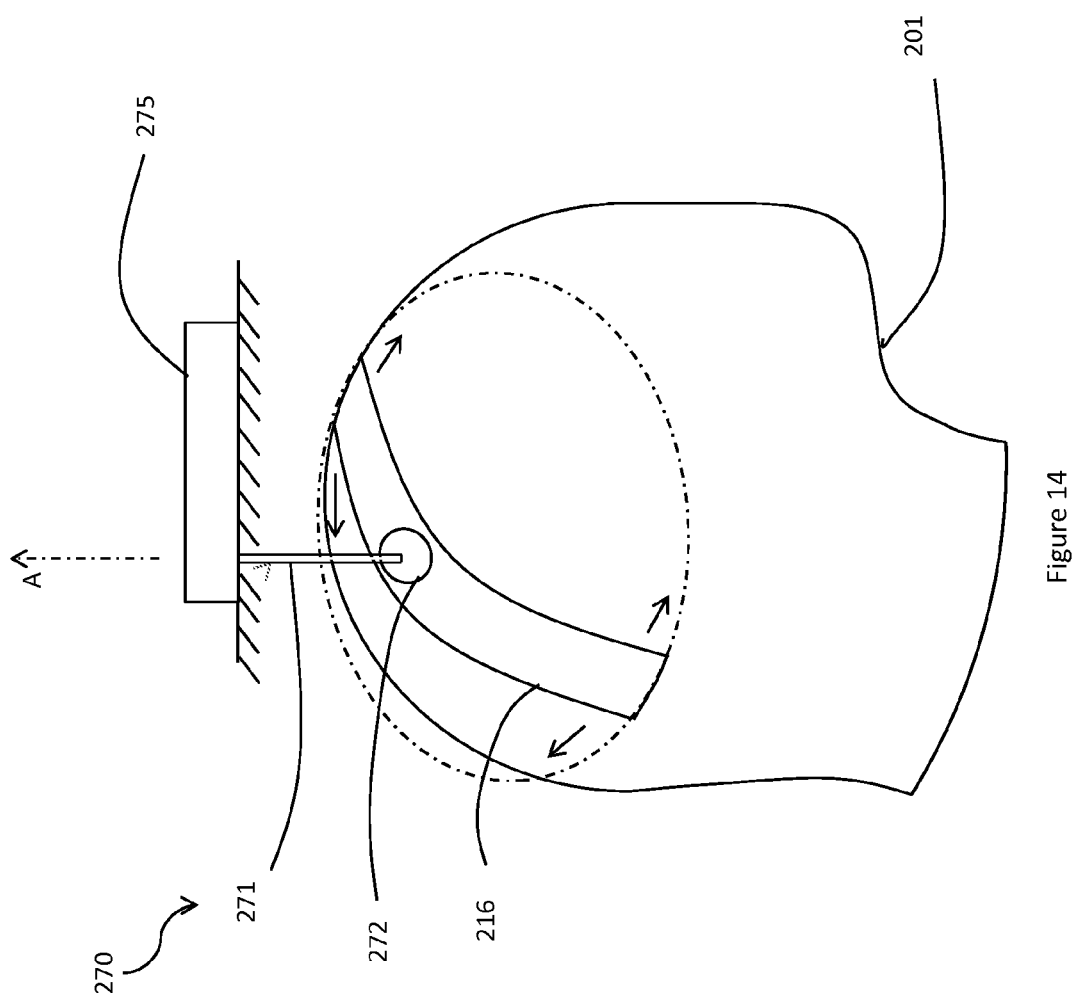

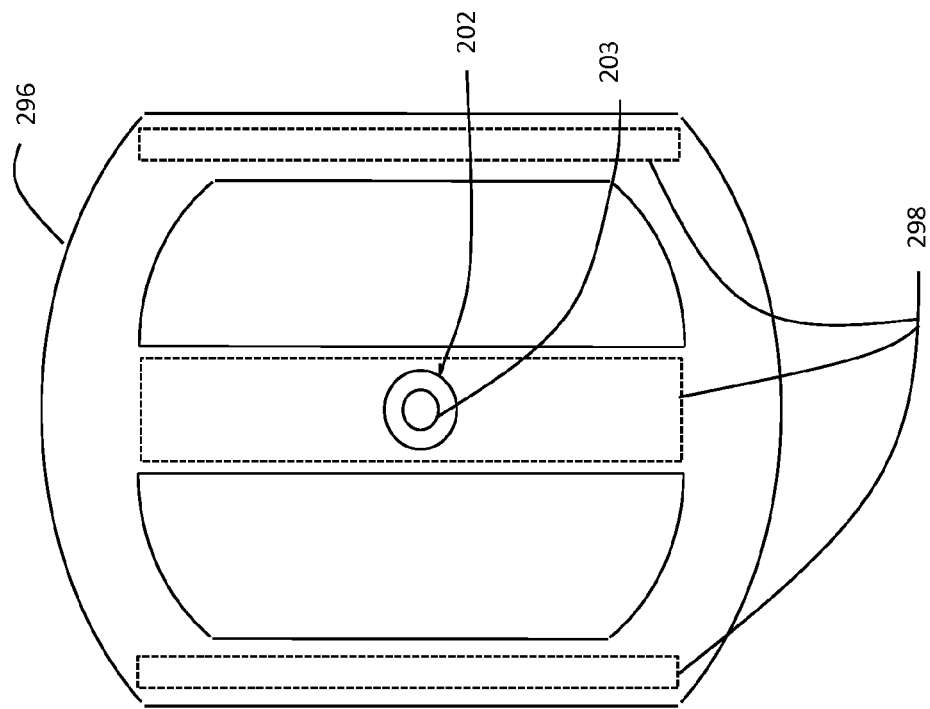
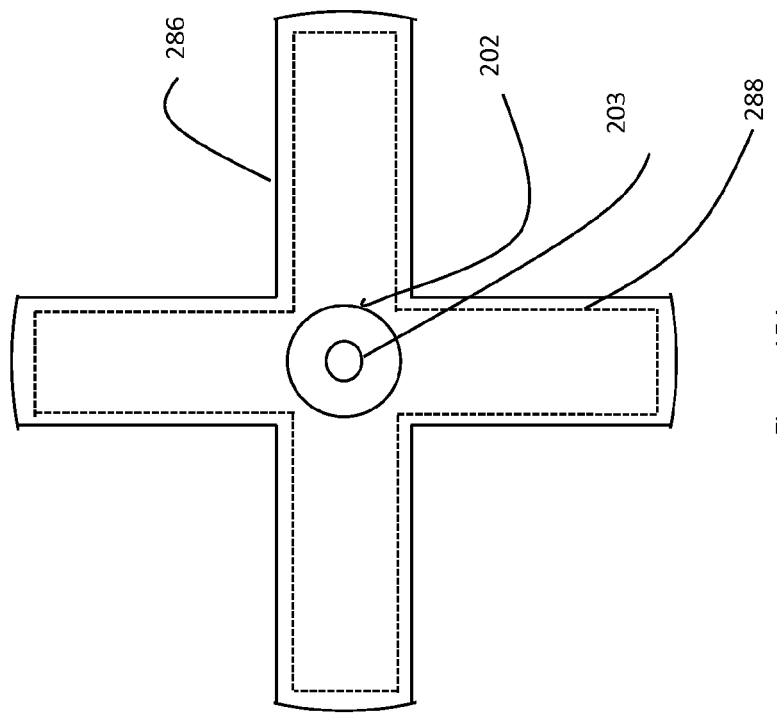

APPARATUSES AND METHODS FOR LASER LIGHT THERAPY OF HAIR

CROSS REFERENCE TO RELATED APPLICATIONS

This application claims the benefit of U.S. Provisional Patent Application No. 61/937,276, filed Feb. 7, 2014, the entire contents of which are hereby incorporated by reference.

FIELD

The various embodiments described herein relate to apparatuses and methods for laser light therapy of hair, and more particularly relate to apparatuses and methods for a laser light therapy brush and a laser light therapy helmet for the prevention and treatment of hair loss.

BACKGROUND

Androgenetic alopecia (AGA) or "baldness" occurs in over 80% of the human population during their lifetime. Accordingly, this condition affects hundreds of millions of people worldwide. Over the years, there have been many attempts at treating hair loss with varying results. One of these attempts to treat AGA includes low-level laser therapy (LLLT) with various mixed results.

SUMMARY

The following is provided to introduce the reader to the more detailed discussion to follow and it is not intended to limit or define any claimed or as yet unclaimed subject matter. One or more groups of claimed or unclaimed subject matter may reside in a combination or a sub-combination of the elements or process steps as described in any part of this document including its claims and figures.

In one broad aspect, in at least one embodiment described herein, there is provided a laser therapy device comprising: an emitter array housing having an active surface with at least one concave shape, the active surface being adapted to face a treatment surface of a user for treating hair loss during use; a plurality of bristles mounted to the emitter array housing and extending outwardly from the active surface; a light therapy module positioned at least partially within the emitter array housing, the light therapy module having: a plurality of emitters for emitting coherent light away from the active surface at a wavelength suitable for treating hair loss; a variable control module coupled to the emitters for controlling the emitters; and a power module coupled to the variable control module for powering the emitters, wherein the bristles and the emitters are arranged in a plurality of rows and in each row the emitters and bristles are arranged substantially linearly.

In at least some of the embodiments, at least one of the rows comprise at least one emitter and at least two bristles arranged on either side of the at least one emitter.

In at least some embodiments, the device comprises a plurality of modes of operation for delivering varying amounts of light energy to the treatment surface of the user, wherein a mode of operation is chosen based on an amount of hair loss experienced by the user to more effectively tailor the treatment to the user's amount of hair loss.

In some embodiments, in a first mode of operation, at least one of the plurality of emitters is controlled to emit coherent light continuously, and at least a second one of the plurality of emitters is controlled to emit coherent light in a pulsed fashion.

In some embodiments, in a second mode of operation the variable control module is configured to sequence the emitters, wherein sequencing the emitters comprises sequentially activating and deactivating rows of emitters, such that at least one band of light energy is emitted along the rows of emitters.

In some embodiments, the sequencing comprises deactivating at least one row of emitters and activating at least one adjacent row of emitters.

In some embodiments, the at least one band of light energy is emitted along a plurality of adjacent rows of emitters, and wherein sequencing comprises deactivating at least one of the plurality of adjacent rows of emitters and activating at least one row of emitters adjacent to the plurality of rows of activated emitters.

In some embodiments, in a third mode of operation, every emitter in the plurality of emitters is controlled to emit coherent light continuously.

In some embodiments, in a fourth mode of operation, every emitter in the plurality of emitters is deactivated.

In some embodiments, the device further comprises a user interface to allow a user to select between the modes of operation.

In some embodiments, the variable control module further comprises: a control unit for generating control signals; and a switching network coupled between the plurality of emitters and the control unit for receiving the control signals in order to switch at least one emitter between an active state and an inactive state during use according to the mode of operation.

In some embodiments, the housing is shaped as a brush.

In some embodiments, the housing is shaped as a helmet.

In some embodiments, the device comprises a rotational coupling coupled to the emitter array housing; a mount configured to receive a portion of the rotational coupling; and an actuator coupled to the rotational coupling configured to rotate the emitter array housing with respect to the mount during use.

In some embodiments, the actuator is rigidly coupled to the mount or to the emitter array housing.

In some embodiments, the mount comprises a spacer for resting the device on a portion of the user, such that the active surface is in a spaced relationship with the user treatment surface.

In some embodiments, the mount comprises a circumferential guide track and the emitter array housing comprises a guide in mating relationship with the guide track, and wherein in use the actuator displaces the guide to rotate the emitter array housing relative to the mount.

In some embodiments, the housing is spaced vertically from the mount.

In some embodiments, the mount rests on a support, such that the mount supports the weight of the device.

In another broad aspect, in at least one embodiment described herein, there is provided a laser therapy device comprising an emitter array housing having an active surface, the active surface being adapted to face a treatment surface of a user for treating hair loss during use; a light therapy module positioned at least partially within the emitter array housing, the light therapy module having: a plurality of emitters for emitting coherent light away from the active surface at a wavelength suitable for treating hair loss; a variable control module coupled to the emitters for controlling activity of the emitters; and a power module coupled to the variable control module to provide power to the emitters; and a user interface coupled to the light therapy module to allow a user to select from a plurality of modes of operation for delivering varying amounts of light energy to the treatment surface of the user, wherein a mode of operation is chosen based on an amount of hair loss experienced by the user to more effectively tailor treatment to the user's amount of hair loss.

In some embodiments, operating the emitters according to a first sequence comprises deactivating at least one row of emitters and activating at least one adjacent row of emitters.

In some embodiments, operating the emitters according to a second sequence comprises activating rows of emitters that are not adjacent to one another.

In some embodiments, the plurality of emitters are sequenced to move the at least one light band relative to the active surface during use by activating and deactivating at least one of the plurality of rows of emitters along a common direction wherein the rows of activated emitters are adjacent to one another or are separated by at least one row of deactivated emitters.

In another broad aspect, in at least one embodiment described herein, there is provided a use of a light therapy device defined having a plurality of modes of operation in accordance with the teachings herein, wherein the use comprises: assessing a user's current hair loss; selecting one or more modes of operation for the light therapy device based on the user's current hair loss to deliver an optimum amount of light energy to a treatment surface of the user, such that the use is tailored to the user's amount of hair loss; activating the light therapy device according to one of the one or more modes of operation; and directing the light therapy device towards the treatment surface.

In at least some embodiments, the use further comprises moving the light therapy device across the treatment surface while the device is activated.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

DRAWINGS

For a better understanding of the various embodiments described herein, and to show more clearly how these various embodiments may be carried into effect, reference will be made, by way of example, to the accompanying drawings which show at least one example embodiment and the figures will now be briefly described.

FIG. 1 is a bottom view of an example embodiment of a laser therapy brush device;

FIG. 2 is a cross-sectional side view of the laser therapy brush device of FIG. 1;

FIG. 3 is another cross-sectional view of the laser therapy brush device of FIG. 1;

FIG. 4 is a cutaway bottom view of the laser therapy brush module of FIG. 1;

FIG. 5 is a cutaway bottom view of an alternative embodiment of the laser therapy brush module of FIG. 1;

FIGS. 6A-6C illustrate an example of a sequential activation mode of operation in which a band representing activated laser emitters propagates through the rows of emitters over time for the laser therapy brush module of FIG. 1;

FIG. 14 is a perspective view of an example embodiment of a ground-coupled or suspended laser therapy helmet;

FIG. 15A is a top view of an example of an alternative embodiment of a laser therapy helmet emitter array housing;

FIG. 15B is a top view of an example of another alternative embodiment of a laser therapy helmet emitter array housing;

Figure 17:
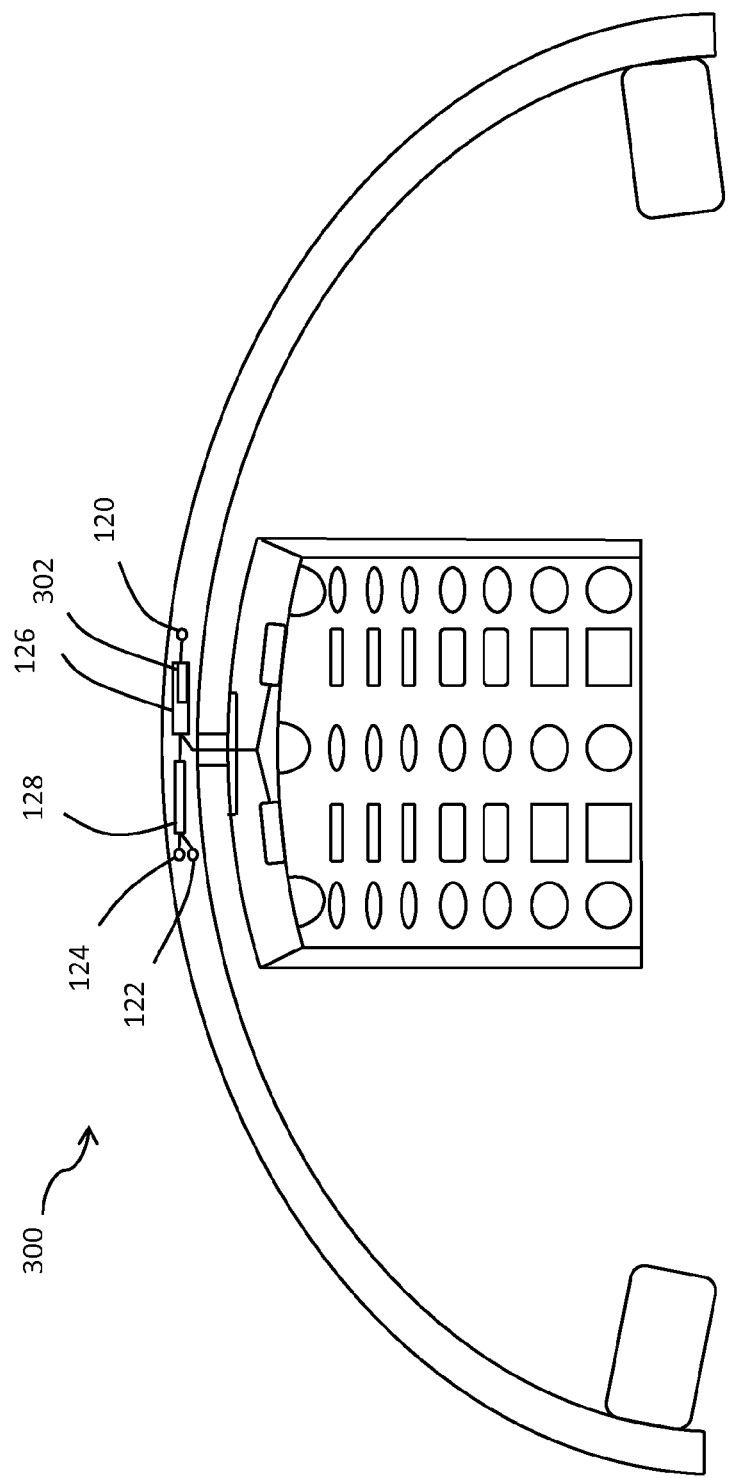

FIG. 17, in a sectional front view, illustrates a variable laser therapy helmet module.

Figure 18C:
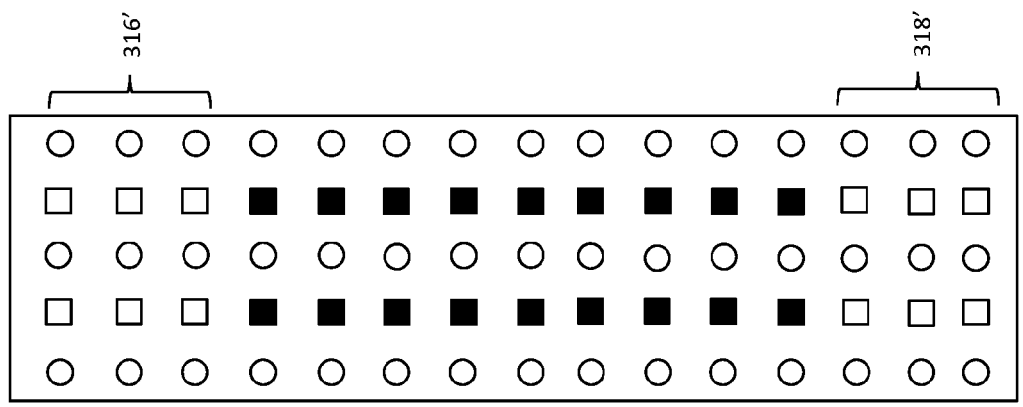
Figure 18B:
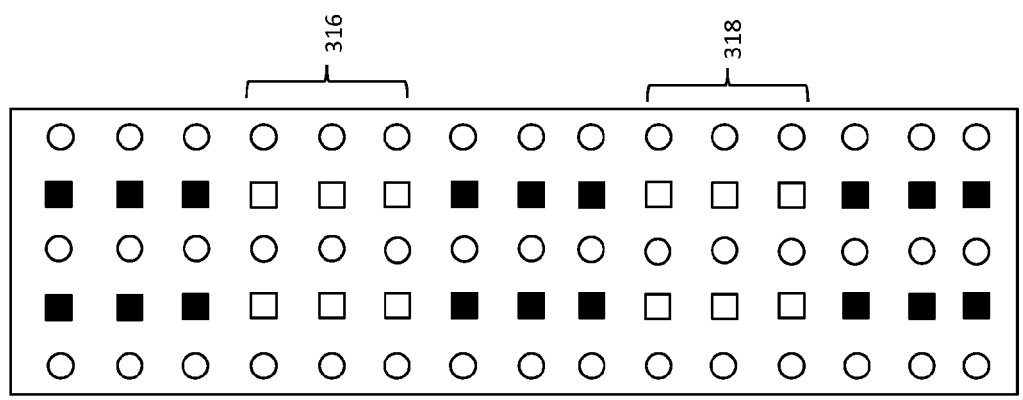
Figure 18A:
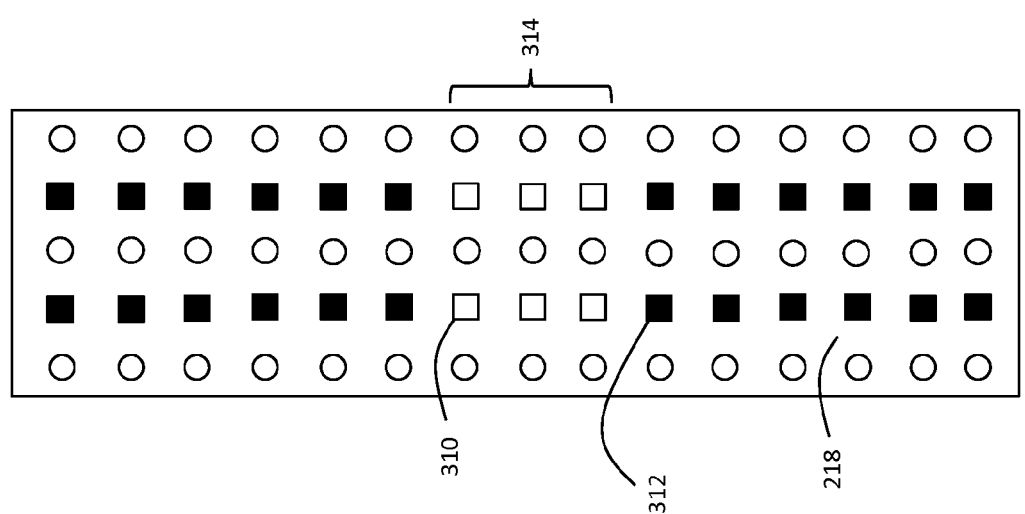
Figure 19B:
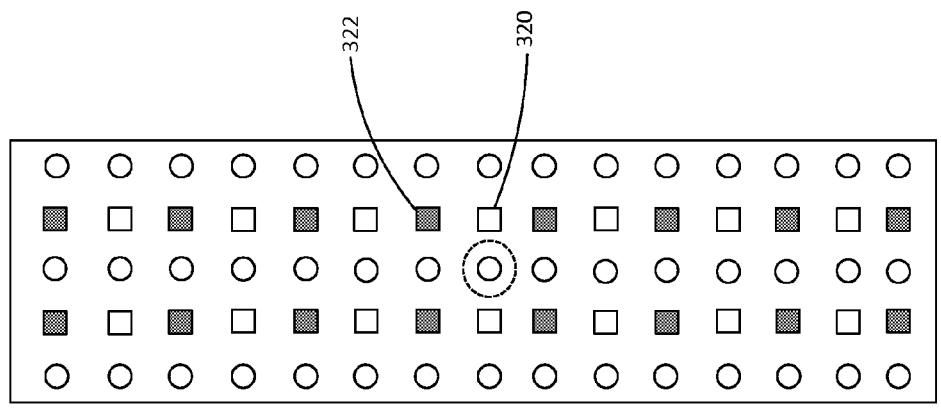
Figure 19A:
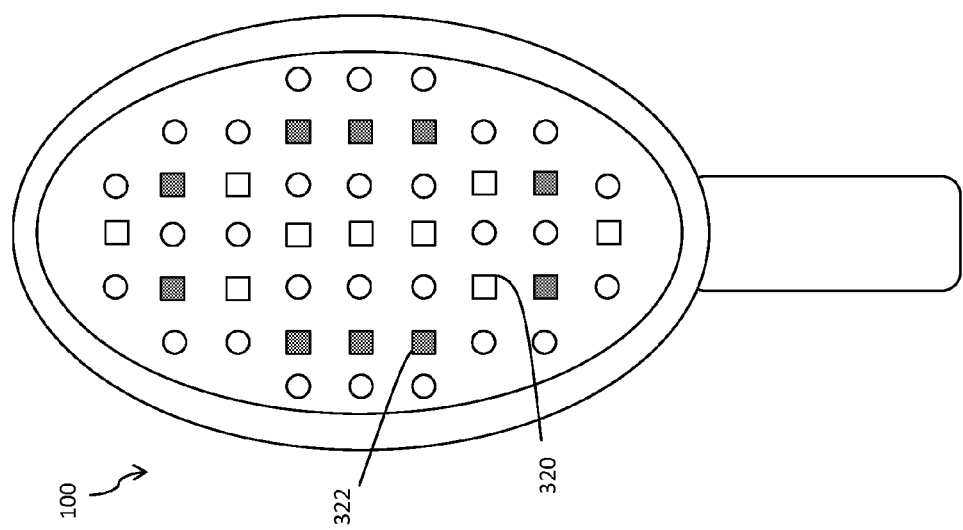
Figure 20:
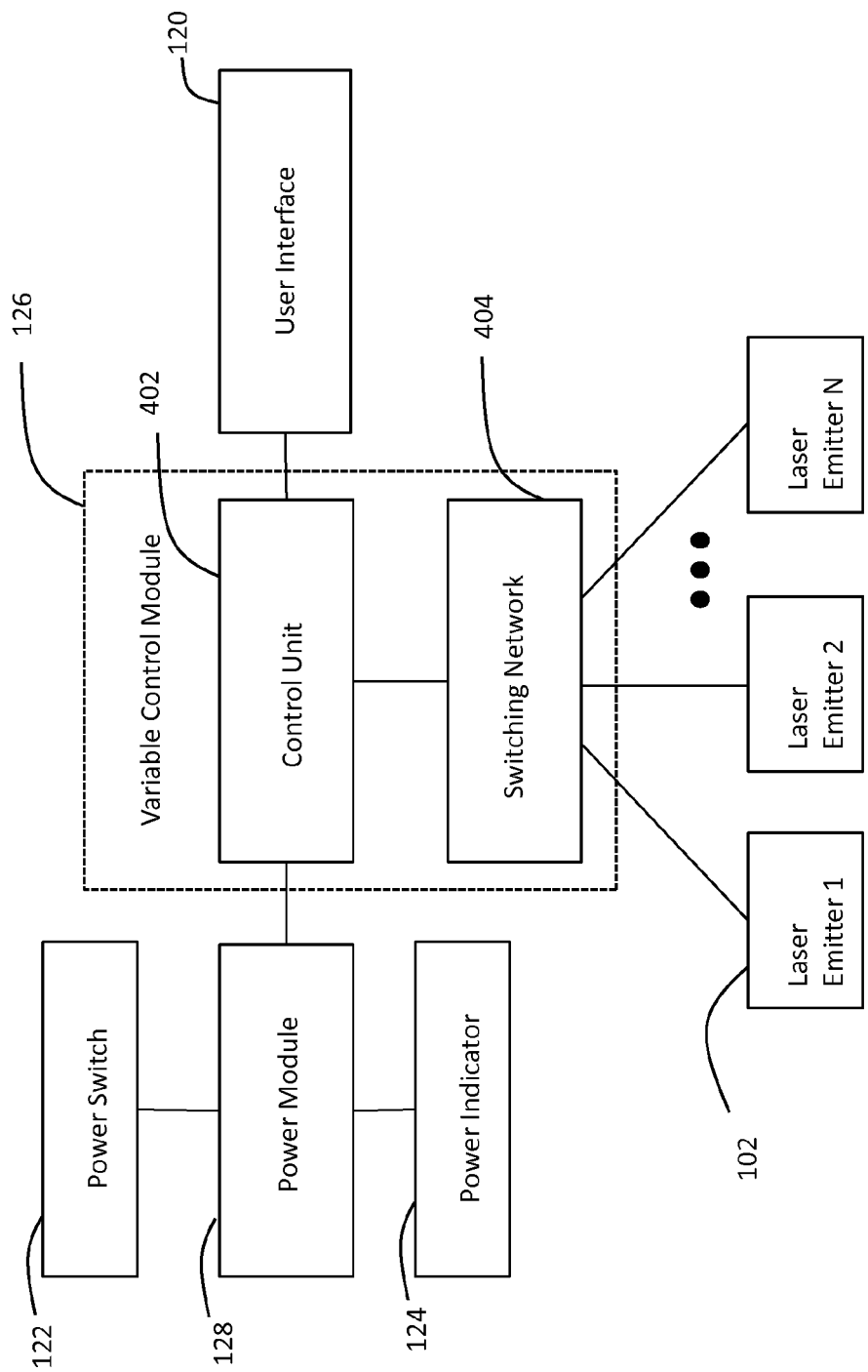
Figure 21:
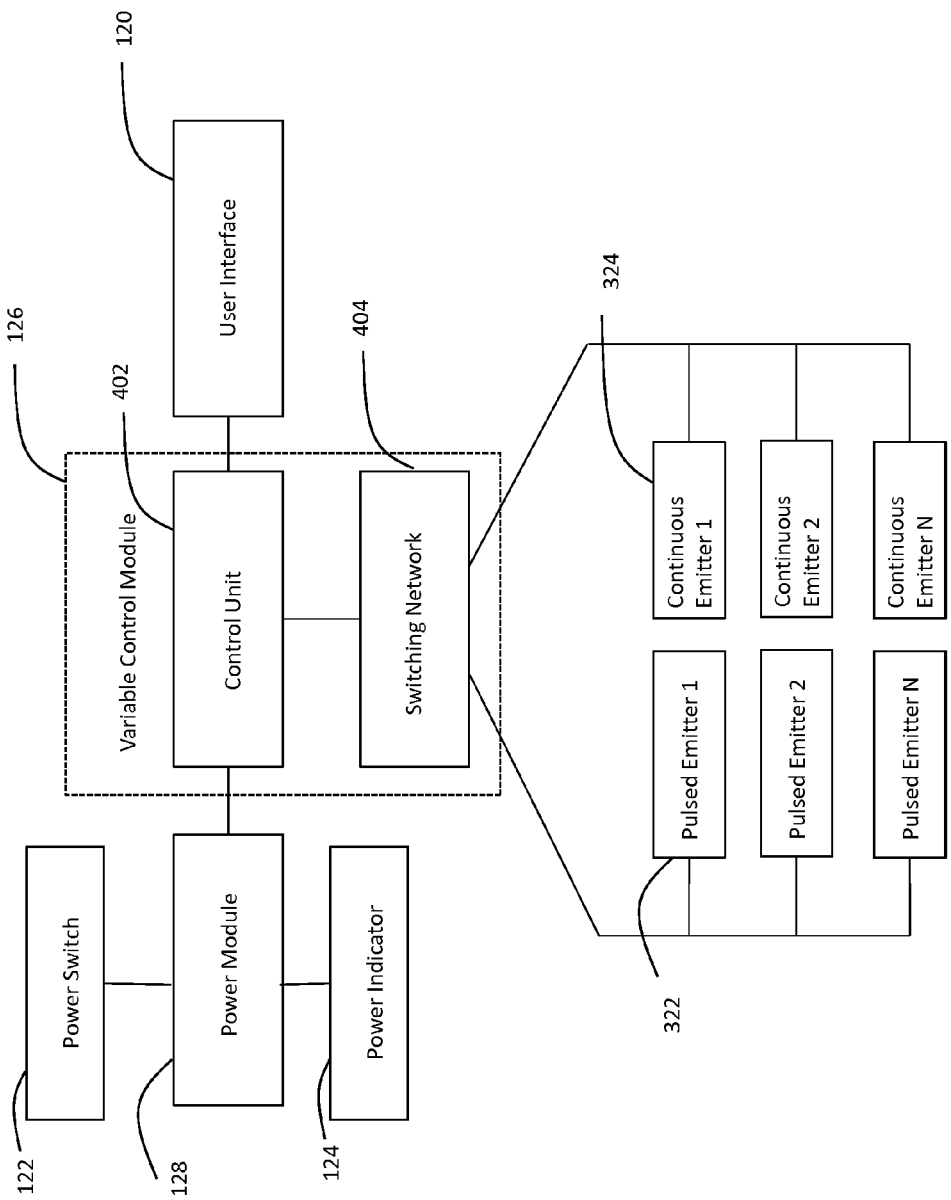
Figure 22:
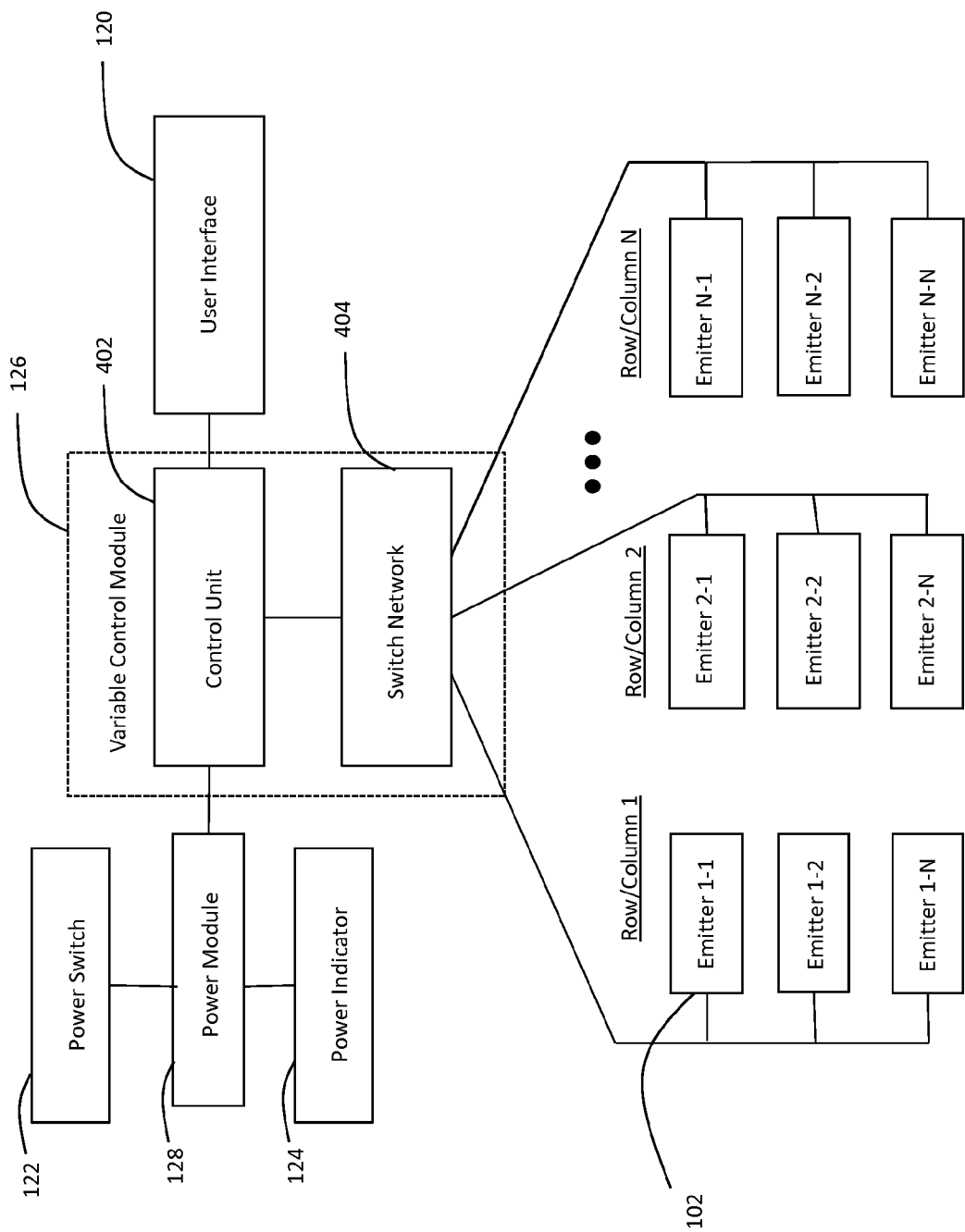

FIGS. 18A-18C illustrate an example of a sequential activation mode of operation in which a band representing activated laser emitters propagates through the rows of emitters over time for a laser therapy helmet;

FIG. 19A is a bottom view showing an example mode of operation for a laser therapy brush device that comprises at least one pulsing laser emitter and at least one continuous laser emitter;

FIG. 19B is a plan view showing an example mode of operation for a laser therapy helmet that comprises a plurality of pulsing laser emitters and a plurality of continuous laser emitters;

FIG. 20 is a block diagram of an example embodiment of a laser emitter module that may be used with a laser therapy brush or helmet device described herein;

FIG. 21 is a block diagram of the laser emitter module of FIG. 20 when the laser emitters are configured as groups of pulsed emitters and continuous emitters; and FIG. 22 is a block diagram of the laser emitter module of FIG. 20 when the laser emitters are grouped in rows for sequential activation.

Further aspects and features of the embodiments described herein will appear from the following description taken together with the accompanying drawings.

DESCRIPTION OF VARIOUS EMBODIMENTS

Various apparatuses or processes will be described below to provide an example of at least one embodiment of claimed subject matter. No embodiment described below limits any claimed subject matter and any claimed subject matter may cover processes, apparatuses, devices, or systems that differ from those described below. The claimed subject matter is not limited to apparatuses, devices, systems, or processes having all of the features of any one apparatus, device, system, or process described below or to features common to multiple or all of the apparatuses, devices, systems, or processes described below. It is possible that an apparatus, device, system, or process described below is not an embodiment of any claimed subject matter. Any subject matter that is disclosed in an apparatus, device, system, or process described below that is not claimed in this document may be the subject matter of another protective instrument, for example, a continuing patent application, and the applicants, inventors, or owners do not intend to abandon, disclaim, or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Androgenetic alopecia (AGA) or "baldness", often referred to as Male Pattern Hair Loss (MPHL) in men and Female Pattern Hair Loss (FPHL) in women, occurs in over 80% of the human population during their lifetime (Unger, 2003). In European men, for example, AGA affects between 29-40% of men aged 18-59 years old, with 30% of men aged 35 or older reporting "moderate hair loss" (Budd, 2000). In the U.S., hair loss occurs in 53% of men by age 40-49, and in 40% of women by age 40 (Leavitt, 2006). In this description, the terms AGA, hair loss, baldness, MPHL and FPHL may be used interchangeably.

Low Level Light Therapy (LLLT) is an emerging technology that has been developed to prevent hair loss, stimulate hair regrowth in areas of hair loss and strengthen hair for a certain percentage of users (Unger, 2003). The inventor, who has long been involved with the development of LLLT both as a Medical Director and a Medical Consultant for several companies that develop light therapy products, has found that while an optimal dosage of LLLT will usually lead to bio-stimulation having the above-described beneficial effects on a user's hair, overstimulation will not lead to any beneficial effects and may actually have detrimental effects. Overstimulation can be caused by treatment with devices having too many laser diodes, or alternately by treatments that are too long or too frequent. The inventor has found that it is beneficial to get the right amount of energy to the user's treatment surface and that it is beneficial to part the user's hair such that the LLLT energy is properly delivered to the user's treatment surface, which will usually be the scalp, but may be different areas for different users. The various embodiments described herein relate to LLLT devices and methods for providing an optimal amount of LLLT to a user's treatment surface, such that bio-stimulation results without causing overstimulation.

Reference is now made to FIGS. 1 to 3, which illustrate an embodiment of a laser therapy brush device 100. The brush device 100 comprises an emitter array housing 108, an emitter array active surface 106, a plurality of laser emitters 102, a plurality of bristles 104 and a handle 109. The emitter array active surface 106 is a concave surface of the housing 108. The emitters 102 and the bristles 104 are mounted to the housing 108 such that the bristles 104 extend outwardly from the active surface 106, and such that the emitters 102, when activated, emit coherent light away from the active surface 106. In at least some embodiments, each emitter 102 emits coherent light outwardly and approximately perpendicularly away from the active surface 106.

The bristles 104 and the emitters 102 are arranged in a plurality of rows wherein at least one of the rows comprises at least one emitter 102 and at least two bristles 104 arranged on either side of the at least one emitter 102 in a substantially linear fashion. For example, row 105 illustrates a particular embodiment of a row. In some embodiments, in each row, each emitter 102 is aligned with two adjacent bristles 104, such that the bristles 104 and the emitters 102 alternate in each row, as illustrated in the example embodiment shown in FIGS. 1 to 3. Henceforth this positioning is referred to as an "aligned alternating arrangement". Although the illustrated embodiments of the brush device 100 illustrate the rows as being perpendicular to the handle 109, a person of ordinary skill in the art would understand that the rows could also be arranged to be parallel to the handle 109, or angled diagonally to the handle 109 in alternative embodiments. Furthermore, although the active surface 106 and housing 108 are shown as being shaped ovally, a person of ordinary skill in the art would understand that the active surface 106 and housing 108 may be otherwise shaped, such as having a circular, hexagonal or rectangular shape in alternative embodiments.

Referring specifically to FIGS. 2 and 3, shown therein are sectional side and end views of the brush device 100. These views show more clearly that the active surface 106 may be concave along two axes, the major and minor axes, such that it is shaped for positioning against a user's treatment surface that may have a convex shape, such as a user's scalp, for example.

In use, the user activates the brush device 100 and positions the active surface 106 against the user's desired treatment surface. The user then moves the brush device 100 across the treatment surface in a direction collinear with the rows of emitters 102 and bristles 104. Alternatively, the user can simply hold the brush device 100 above the treatment surface. In embodiments where the bristles 102 and emitters 104 are arranged in the aligned alternating arrangement, as the brush device 100 moves across the treatment surface, each bristle 104 is closely followed by an emitter 102, which is closely followed by another bristle 104. When used on the user's scalp, this aligned alternating arrangement ensures that the bristles 104 part the user's hair in advance of each emitter 102, such that energy is directly delivered to the treatment surface, instead of being absorbed by the user's hair. Further, the concave shape of the active surface 106 ensures a comfortable mating of the active surface of the brush device 100 with the user's treatment surface, as well as ensuring that the emitters 102 emit coherent light approximately perpendicularly to the user's treatment surface when active in order to optimally deliver energy to the user's treatment surface. Other angles may be used in alternative embodiments where applicable.

The brush device 100 is typically used for the treatment of AGA such that the user's treatment surface is the area of a user's head that experiences hair growth, such as the scalp. In this description, the terms scalp, head or treatment surface may be used interchangeably. However, a person of ordinary skill in the art will understand that other convex surfaces of a user's body may be treated by LLLT; for example, the brush device 100 may be positioned against a user's eyebrow, chin, jawbones, chest, arms or legs.

In most embodiments, the housing 108 may be fabricated from material known to those of ordinary skill in the art as having sufficient rigidity to avoid unwanted flexing during use. In some embodiments, the housing 108 may be made of plastic, rubber, or metal.

In most embodiments, the bristles 104 are sized and shaped to part the user's hair in advance of emitters 102 without creating discomfort for the user. In most embodiments, the bristles 104 will be blunt and will be sized to provide sufficient rigidity to optimally part the user's existing hair in advance of the emitters 102 passing over the treatment surface when the brush device 100 is in use (as described above). In an example embodiment, the bristles 104 may have a height of about ½ an inch, although other dimensions may be used. The bristles 104 may be constructed of a material providing sufficient rigidity to part a user's hair. In some embodiments, the bristles may be made of rubber, plastic, or metal.

In most embodiments, the laser emitters 102 are laser diodes. A person of ordinary skill in the art would understand that other emitters of coherent light may be used. Throughout this description, the terms laser light or coherent light are used interchangeably. In many embodiments, the laser emitters may be configured to output low-level laser light at a wavelength in the range of 600 nm to 1000 nm. However, a person of ordinary skill in the art will understand that the laser emitters may be configured to emit light at other wavelengths suitable for treating hair loss. In particular, the emitters are chosen such that during use enough energy is supplied to the user treatment surface for biostimulation, but not so much as to cause overstimulation. In some embodiments, each laser emitter 102 may be configured to output light energy having 1 to 5 mW of power, for example.

In at least some embodiments, the laser emitters 102 may be configured to output 5 mW of power at a wavelength of 650 nm.

In at least some embodiments, 10-30 laser emitters may be mounted to the housing 108 of the brush device 100. For example, in the illustrated embodiment of FIG. 1, 19 emitters 102 are mounted to the housing 108.

Reference is now made to FIG. 4, which illustrates an example embodiment of a laser therapy module 121 that may be used with the laser therapy brush device 100. The laser therapy module 121 comprises the emitters 102; a variable control module 126 coupled to the emitters 102 for controlling the emitters 102; and a power module 128 coupled to the variable control module 126 for powering the emitters 102. The brush device 100 may further comprise at least one of a user interface 120, a power switch 122, and a power indicator 124. Some or all of these elements may be mounted on one or more printed circuit boards, which may or may not be flexible, and are located in the handle portion 109 and possibly part of the housing 108 of the brush device 100.

The variable control module 126 is generally operable to selectively activate, deactivate or otherwise control individual emitters 102 or emitter groups (e.g. rows of emitters, columns of emitters, or user-determined or predetermined groups of emitters that are grouped together and can be controlled together). In some embodiments, the variable control module 126 comprises a switching network (described in relation to FIGS. 20-22) for activating or deactivating the emitters 102. In such embodiments, the variable control module 126 activates or deactivates the emitters 102 by sending control signals to switches within the switching network. Individual emitters 102 or emitter groups can be coupled to switches in the switching network for individual or group control by the variable control module 126 via control signals. The variable control module 126 may comprise a processor, an ASIC, a hardware controller and the like, which can be programmed or otherwise configured to provide control signals. The variable control module 126 may be provided with software instructions to implement certain functionality.

In at least some embodiments, the variable control module 126 may be operable to provide control signals in order to control the total length of treatment time and therefore the total emission power of the emitters 102, individually or in emitter groups. Treatments lasting 12-15 minutes given three times a week or on alternate days are desirable and preferred.

In at least some embodiments, the variable control module 126 is operable to activate, deactivate or otherwise control the emitters 102 or emitter groups for user-determined or predetermined periods of time. In such embodiments, the variable control module 126 may be operable to activate and/or deactivate or otherwise control the emitters 102 or emitter groups according to user-determined or pre-determined timed sequences and/or durations of time (to limit treatment time).

Accordingly, it should be understood that in at least some embodiments the variable control module 126 has control over the activation, deactivation, and timing for laser light emitted by the emitters.

However, in at least some embodiments the variable control module 126 may only have limited control over the emitters 102. For example, in some embodiments, the variable control module 126 may be operable to only control the activation and deactivation of the emitters 102 or the emitter groups.

The user interface 120 may be coupled to the variable control module 126 to allow the user to select a mode of operation of the brush device 100. In some embodiments, each mode of operation delivers a different amount of light energy to the user's treatment surface. Accordingly, a user may select a mode of operation based on an amount of hair loss experienced by the user in order to more effectively treat the hair loss for that particular user. This is beneficial since hair blocks at least some light energy from reaching the user's treatment surface, and therefore if a user has less hair, it may be beneficial to select a mode of operation wherein less energy is output to the user's treatment surface in order to prevent overstimulation.

In at least some embodiments, the user interface 120 is operable to select between four modes of operation including a first mode in which all emitters are deactivated; a second mode in which all emitters are activated and emit light continuously; a third mode in which at least one emitter of the plurality of emitters emits coherent light in a pulsed fashion; and a fourth mode in which the variable control module 126 sequentially activates and deactivates rows of emitters, such that at least one band of light energy propagates along the rows of emitters.

As in most embodiments the mode of sequential activation emits less total energy than the mode with a combination of pulsing and continuous emitters. The mode of sequential activation is best suited for patients with a small amount of remaining hair (thin hair) to prevent overstimulation, whereas the mode with a combination of pulsing and continuous emitters is best suited for patients with moderate hair loss. As the mode with the continuous emitters produces more total output energy (e.g. 5 mW of output power for each of 19 diode lasers provides 95 mW of output power), than the mode with a combination of pulsing and continuous emitters (e.g. 50 mW of output power from 10 continuous 5 mW emitters, and 22.5 mW of output power from 9 pulsed 5 mW emitters operating only half the time, provides 72.5 mW of total output power), the mode with continuous emitters is best suited for patients with early or minimal hair loss.

In this way the various modes of treatment allow for tailoring of the total energy and power output to each individual during a treatment session, which results in better-controlled bio-stimulation without overstimulation. These modes of operation are further discussed with respect to FIG. 6, and 18-22. It should be understood that these modes of operation may apply to any of the various embodiments of the brush device 100 and/or a helmet device, including, for example, the helmet devices 200, 230, 250 and 270 described herein.

In at least some embodiments, the user can interact with the user interface 120 to modify user-determined settings, such as desired treatment time, or the total power of the emitters 102 or emitter groups, which may be selected to more optimally treat the user's amount of hair loss.

In some embodiments, a user can modify the modes of operation using the user interface 120 to enter user-determined settings of operation for the modes of operation. For example, the user can modify which emitters should be pulsed in the pulsed mode of operation, and/or can modify the rate of pulsing. Further, in some embodiments, the user can modify the width and/or pattern of the bands of activated emitters in the sequential mode of operation. Further, in some embodiments, the user can modify the treatment time associated with each mode of operation.

In some embodiments, the user can modify the modes of operation by connecting the brush device 100 to a computing device (not shown) and modifying the modes of operation by using the computing device's user interface. In embodiments where the user can modify the modes of operation using a computing device, the laser therapy module 121 comprises a communication module (not shown), such as a USB port, a parallel port, a serial port, a wireless radio and the like, for communication with the computing device, using a corresponding communication scheme as is known by those of ordinary skill in the art.

In alternative embodiments, the device settings and modes of operation can only be modified after the user enters a password, such that modification of the device settings is only carried out in consultation with a light-therapy physician or practitioner who knows the password. In such an embodiment, the user may enter a password before modifying the device settings. The password may be preset before the device is sold to customers, such that a purchaser of the device does not necessarily know the password for the device ahead of time but may be given the password in a device manual that may be sold with the device or an invoice or a separate communication once the device is purchased by the user. In such embodiments, the variable control module 126 may comprise a processor, an ASIC, a hardware controller or the like, which can be programmed or otherwise configured to modify the settings and modes of operation according to manipulation of the user interface 120 by a user. The variable control module 126 may be provided with software instructions to implement the functionality The power module 128 is coupled to the power switch 122 and the power indicator 124. The power switch 122 may be a switch, a button or any other means known to those of ordinary skill in the art such that the user can manipulate the power switch 122 to activate or deactivate the brush device 100. In some embodiments, the user interface 120 may be coupled to the power switch 122, such that the user activates the brush device 100 by using the user interface 120. The power indicator 124 generally indicates if the brush device 100 is activated and the power indicator may be an LED or other suitable element as is known to those skilled in the art.

In some embodiments, the power module 128 comprises a self-contained power unit, such as a battery, which may or may not be rechargeable. In such embodiments, the power indicator 124 may also be implemented to indicate the remaining power stored in the self-contained power unit with a visual, audible or tactile cue.

Alternatively, in some embodiments, the power module 128 may be coupled to an external power source 130, such as an electrical outlet as in laser therapy module 131, shown in FIG. 5.

Alternatively, in some embodiments, the power module 128 may comprise a self-contained power unit, and is additionally connectable to an external power source 130, e.g. for charging a self-contained power unit.

It should be understood that in these various embodiments, the power module 128 further comprises electrical components to adjust the voltage that is supplied to power the device. For example, a transformer and/or switched mode power supply may be used. Furthermore, it should be understood that the power module 128 further comprises electrical components to ensure that the brush device 100 is safe for use. For example, fuses, current limiters, insulative material and the like may be used as is known to those skilled in the art.

Reference is now made to FIGS. 6A-6C, which illustrate steps in a mode of operation of the brush device 100 for which there is sequential activation of emitters 102 during use. As explained above, the user interface 120 allows a user to select a mode of operation of the brush device 100. FIGS. 6A, 6B and 6C illustrate successive steps of a mode of operation of the brush device 100 in which a band of light due to the activated groups of laser emitters 143, 143', and 143" propagates through the rows of emitters 102. In this mode of operation, the variable control module 126 controls the emitters 102 such that adjacent emitters 102 in one or more rows or emitter groups of one or more rows of emitters 102 are sequentially activated in successive steps so that a band of emitted light propagates across the active surface 106 of the brush device 100. For example, FIGS. 6A-6C show bands of emitters 143, 143', 143", respectively, in which three rows of emitters are being activated during a given step. In FIGS. 6A-6C, the activated emitters are shown with reference numerals 140 and are not shaded while the inactive emitters are shown with reference numerals 142 and are colored black.

In alternate embodiments, there may be different patterns of emitted light due to a particular sequential activation of the emitters 102 or emitter groups. For example, in some embodiments, two rows of emitters may be activated during a given step. Furthermore, in another alternative, more than one row of activated emitters may be activated during a step, where one row of activated emitters is not adjacent to another row of activated emitters. For example, two separated rows of emitters may be active with one inactive row of emitters in between. Further, in other embodiments, the number of rows of activated and deactivated emitters for one sequencing may be changed.

In alternative embodiments, there may be overlap in the active rows of emitters between adjacent steps. For example, while FIG. 6A shows that three rows of emitters are active in the first step and three adjacent rows are activate in the next step (FIG. 6B), in some alternative embodiments only one of the three rows may be deactivated and only one adjacent row may be activated between adjacent steps. For example, in an alternative embodiment, the first step of the sequence may be as is shown in FIG. 6A, but in the second step, the bottom row of emitters for emitter group 143 is inactive, the top two rows of emitters for emitter group 143 are active and the bottom row of emitters for emitter group 143' is active. Further steps may proceed in the same manner such that at least one active light band propagates across the active surface 106 during use.

In some alternative embodiments, the band of activated emitters may instead comprise a column of emitters or a diagonal line of emitters.

In some alternative embodiments, the number of rows in a band of active emitters or the time between steps can be modified by the user.

It should be noted that for the mode of operation described with respect to FIGS. 6A-6C and the various alternatives just described, this mode of operation generally provides less energy to the treatment surface than if the emitters are continuously activated, such that it is best suited for thin-haired individuals to prevent overstimulation. Additionally, because the groups of activated emitters move in sequential bands instead of random groupings, the user treatment surface may be given more time to recover between receiving doses of light energy.

Figure 8:
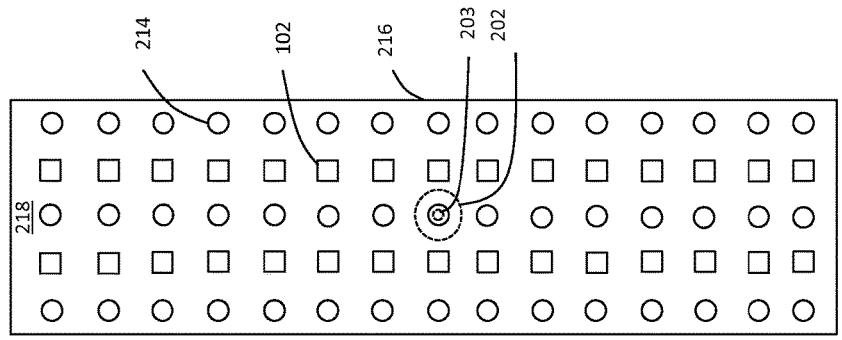
FIG. 8 is a plan view of an example embodiment of a laser therapy helmet emitter array that may be used with the laser therapy helmet of FIG. 7.
Figure 7:
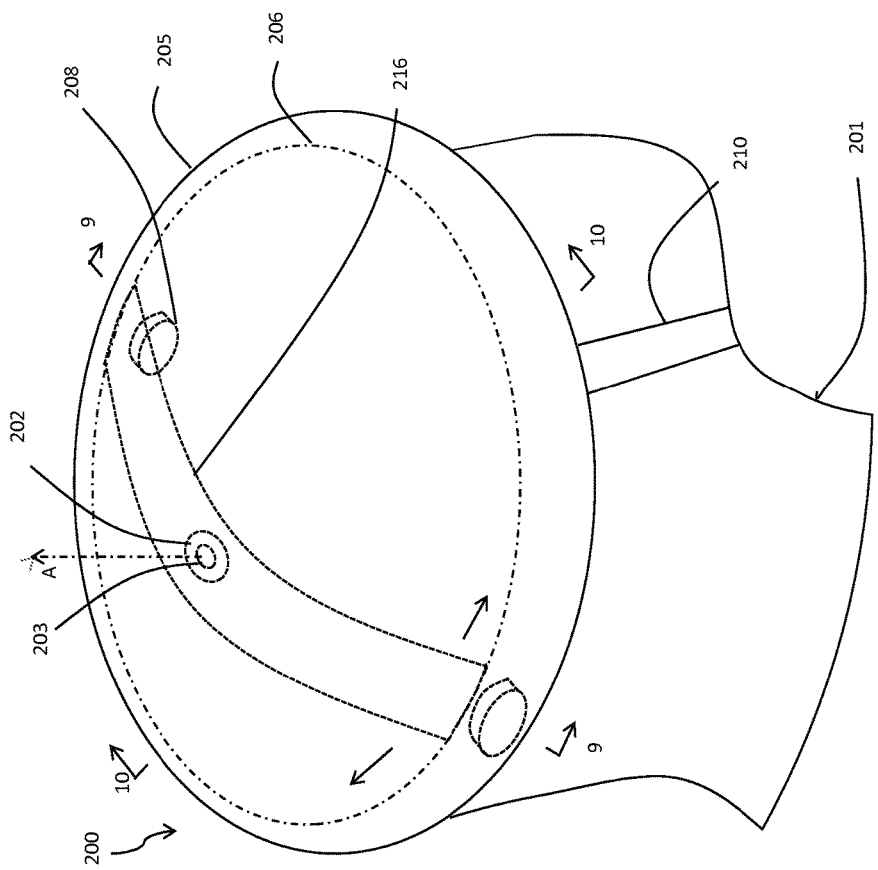
FIG. 7 is a perspective view of an example embodiment of a laser therapy helmet.
Figure 9:
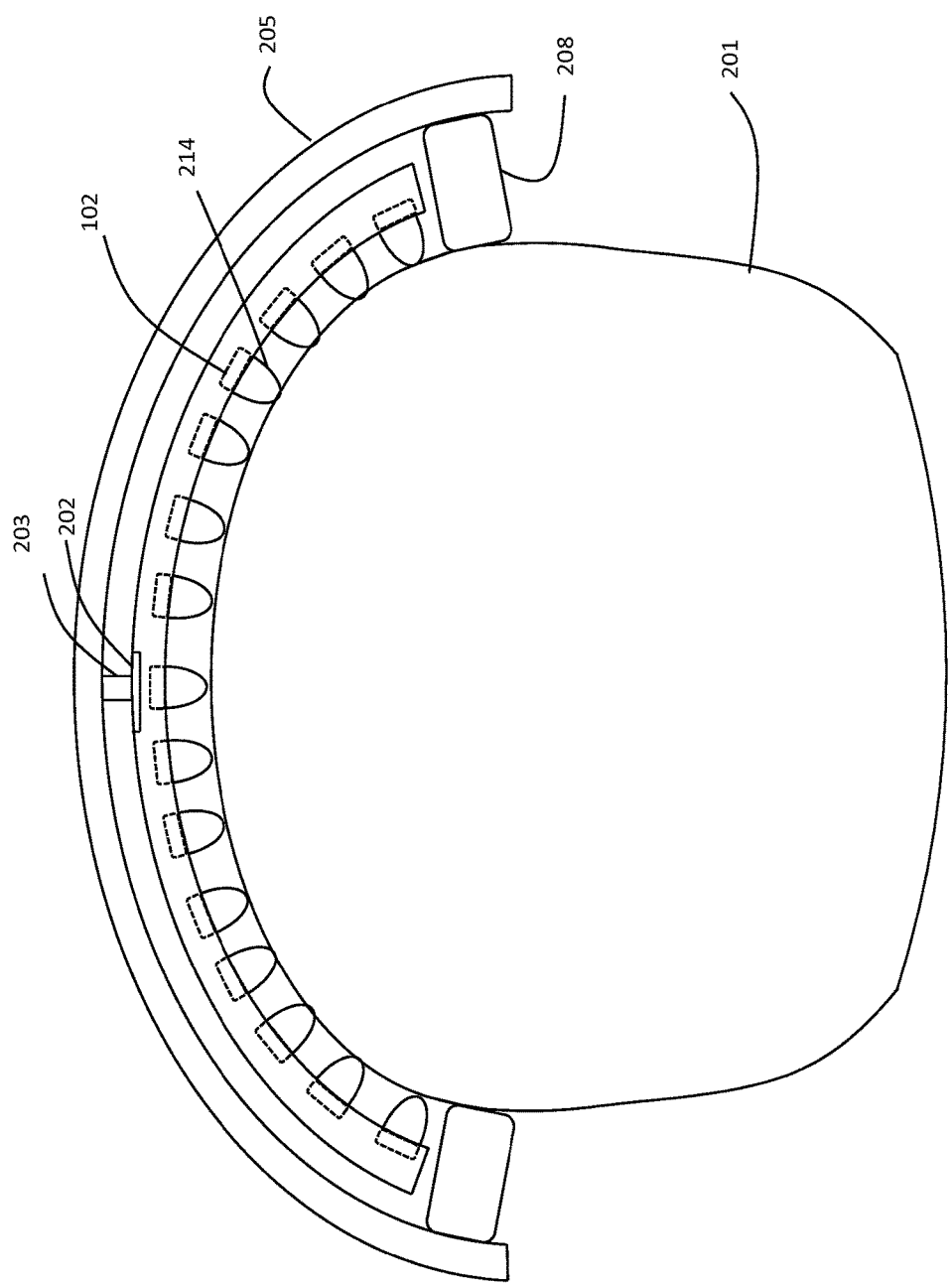
FIG. 9 is a cross-sectional side view of the laser therapy helmet of FIG. 7.
Figure 10:
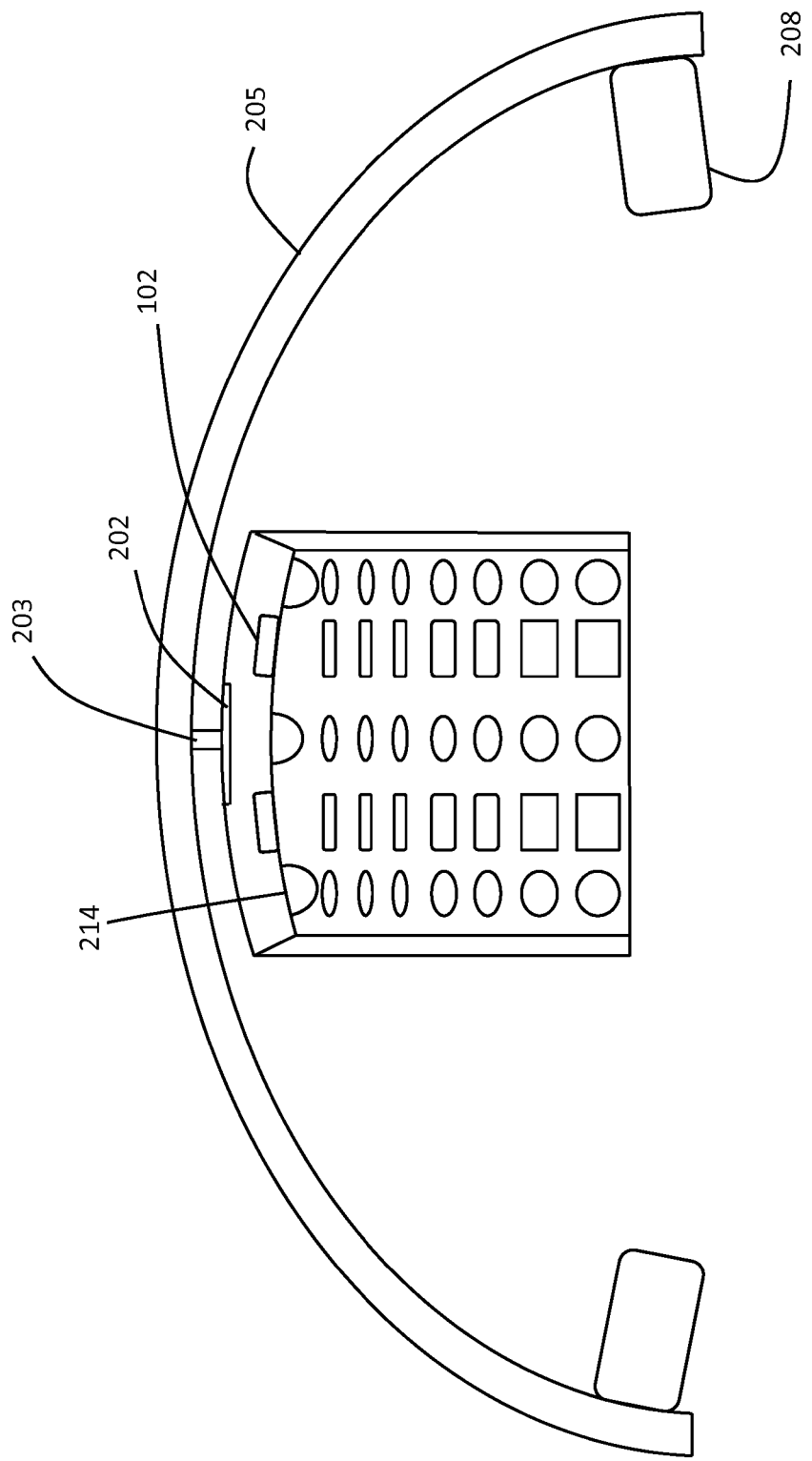
FIG. 10 is a cross-sectional front view of the laser therapy helmet of FIG. 7.
Figure 11:
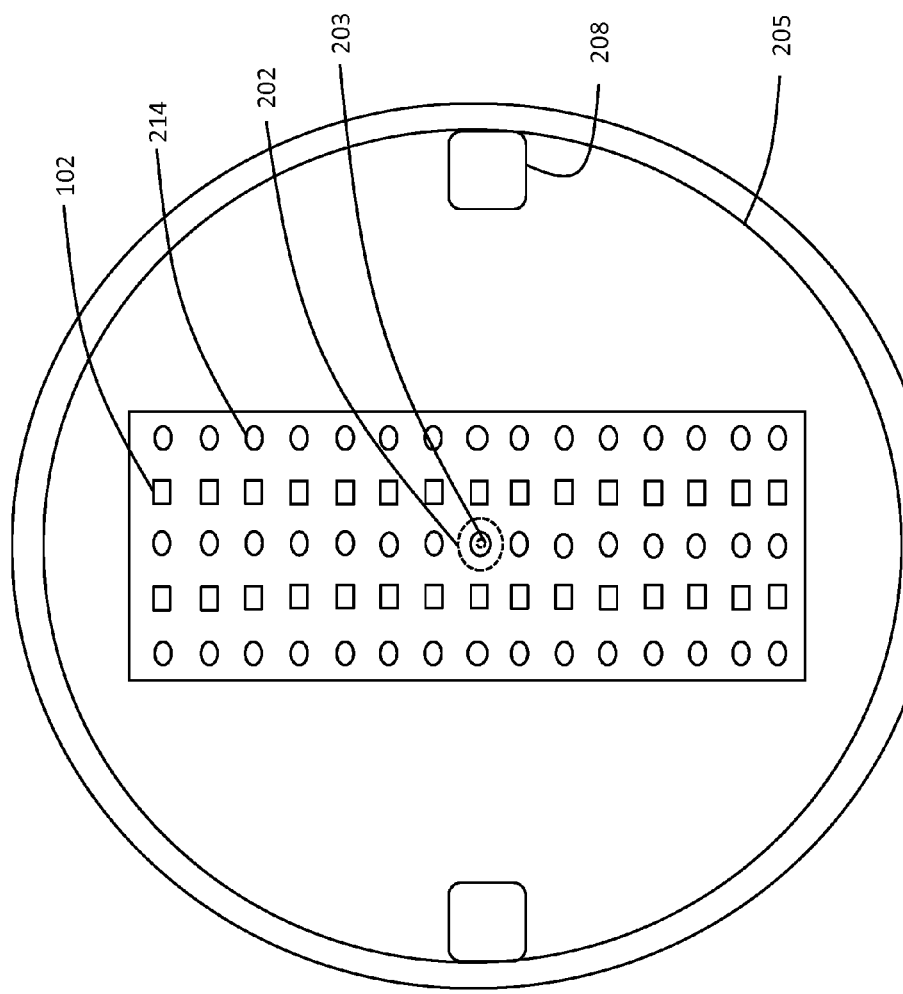
FIG. 11 is a bottom view of the laser therapy helmet of FIG. 7.

Reference is now made to FIGS. 7-11, which illustrate an embodiment of a laser therapy helmet device 200. As in the laser therapy brush device 100, described above, the laser therapy helmet device 200 comprises an emitter array housing 216, an emitter array active surface 218, a plurality of laser emitters 102 and a plurality of bristles 214. FIG. 8 shows a plan view of emitter array active surface 218. The emitter array active surface 218 is a concave surface of the emitter array housing 216, as best shown in FIGS. 9-11.

The emitters 102 and the bristles 214 are mounted to the emitter array housing 216 such that the bristles 214 extend outwardly from the emitter array active surface 218 towards the user's treatment surface (when the device 200 is in use), and such that the emitters 102, when activated, emit coherent light away from the active surface 218 towards the user's treatment surface (when the device is in use). The bristles 214 and the emitters 102 may be arranged in the same manner as the bristles 104 and the emitters 102, described in relation to FIGS. 1 to 3.

In most embodiments the bristles 214 have the same construction as the bristles 104. The bristles 214 may be suitably varied with regard to the bristles 104 to ensure optimum parting of the user's hair for the helmet device 200, such as by lengthening the bristles 214 to longer than about ½ an inch, for example. In addition, or in the alternative, the helmet device 200 may comprise more emitters 102 than the brush device 100 because the helmet device 200 may comprise a larger active surface 218. In the illustrated embodiments, the helmet device 200 comprises about thirty emitters 102. However, in other embodiments, a different number of emitters 102 may be used.

Although the emitter array housing 216 and the emitter array active surface 218 are shown as being rectangularly shaped, the emitter array housing 216 and the emitter active surface 218 may be shaped differently in alternative embodiments. For example, at least one of the emitter array housing 216 and the emitter active surface 218 may have a circular, oval, or hexagonal shape, or may extend along only half of the arc of the helmet 200, for example. Some example embodiments are described in relation to FIGS. 15A-B.

The laser therapy helmet device 200 also comprises a mount 205, a rotational coupling 203 and an actuator 202. The helmet mount 205 may be coupled to the emitter array housing 216 or may be integral with the emitter array housing 216, depending on the particular embodiment. In the illustrated embodiments, the emitter array housing 216 is rotationally coupled to the mount 205 with the rotational coupling 203. During use, the actuator 202 is operable to rotate the emitter array housing 216 relative to the mount 205 and the user's head 201 (along the path 206 shown in FIG. 7). While the illustrated embodiments show that the actuator 202 is coupled to the emitter array housing 216, in alternative embodiments the actuator 202 may be coupled to the mount 205.

There may be a multitude of embodiments of the rotational coupling 203 and the actuator 202. For example, in at least some embodiments, the rotational coupling 203 may be a shaft with appropriate rotational bearings mounted to the mount 205 and/or the emitter array housing 216. Furthermore, in at least some embodiments, the actuator 202 may be an electric motor with an output shaft coupled directly or indirectly to the rotational coupling 203.

In some embodiments, the helmet 200 also comprises spacer(s) 208 and/or a chin strap 210. The spacer(s) 208 are mounted to the mount 205 to evenly support the helmet 200 on the user's head 201. Although the spacer(s) 208 are shown positioned at the front and back of the mount 205 in FIG. 7, the spacer(s) 208 may also or alternatively be positioned at other locations on the mount 205. The chin strip 210 is coupled to the mount 205 and is looped around the user's chin in use to stably and releasably support the helmet 200 on the user's head 201. In alternative embodiments, other straps or restraints may be used to support the helmet device 200 on the user's head 201.

In some alternative embodiments, the spacer(s) 208 may be suitably varied to support the helmet 200 on other body parts of the user, for example the user's shoulders or back.

In some alternative embodiments, the spacer(s) 208 may be varied to support the helmet 200 on the user's clothing or a mount worn by the user.

In some alternative embodiments, the spacer(s) 208 may be shaped differently to comfortably support the helmet 200 on the user's head 201.

Figure 12:
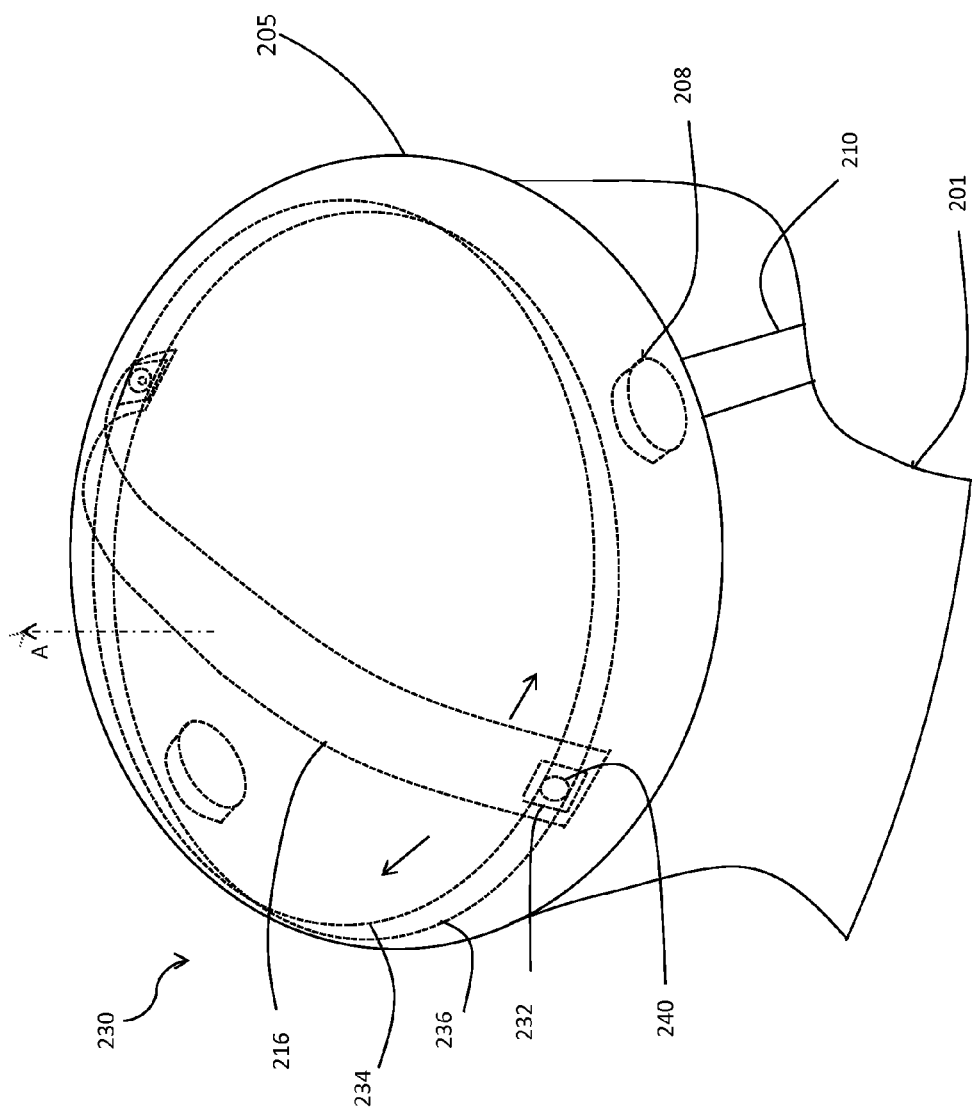
FIG. 12 is a perspective view of an example embodiment of a laser therapy helmet with a guide track.

Reference is now made to FIG. 12, which illustrates another example embodiment of a laser therapy helmet device 230 that uses a guide track to rotate the emitter array housing 216 relative to the helmet mount 205 during use. The helmet 230 comprises a guide track upper edge 234, a guide track lower edge 236, a guide wheel 240, and an actuator 232. In the illustrated embodiment, the actuator 232 is coupled to the emitter array housing 216, and the guide wheel 240 is rotationally coupled to the actuator 232. The mount 205 is coupled to the guide track upper edge 234 and the guide track lower edge 236. In use, the guide track upper edge 234 and the guide track lower edge 236 serve as a guide track for the guide wheel 240. In use, the actuator 232 rotates the guide wheel 240 moving it along the guide track such that the emitter array housing 216 rotates relative to the mount 205 and the user's head 201. The guide wheel 240 is positioned such that it has sufficient friction with the guide track so that the emitter array housing 216 rotates about the mount 205 when the guide wheel 240 is rotated by the actuator 232.

In some embodiments, the guide wheel 240 comprises guide wheel teeth (not shown) while the guide track upper edge 234 and the guide track lower edge 236 comprise grooves (not shown) that releasably mate with the guide wheel teeth in use. The guide wheel teeth cause relative rotation of the emitter array housing 216 about the mount 205 when the guide wheel 240 is rotated by the actuator 232.

In an alternative embodiment, the actuator 232 and the guide wheel 240 may be coupled to the mount 205 and an alternate guide track (not shown) may be affixed to the emitter array housing 216.

In alternative embodiments, the emitter array housing 216 comprises a guide flange (not shown) and the mount 205 comprises a vertical mount surface (not shown). The guide flange may extend from the emitter array housing 216, providing an approximately vertical mounting surface. The vertical mounting surface is an approximately vertical surface of the mount 205 whereupon the guide track may be mounted. In such embodiments, the guide wheel 240 and/or the actuator 232 are mounted to the guide flange. This embodiment provides for smooth rotation of the emitter array housing 216 relative to the mount 205, because the guide track and the guide flange are not angled, such that increased stability is achieved. In alternative embodiments, the guide track may be mounted to the guide flange, and the guide wheel 240 and/or actuator 232 may be mounted to the vertical mount surface.

Figure 13:
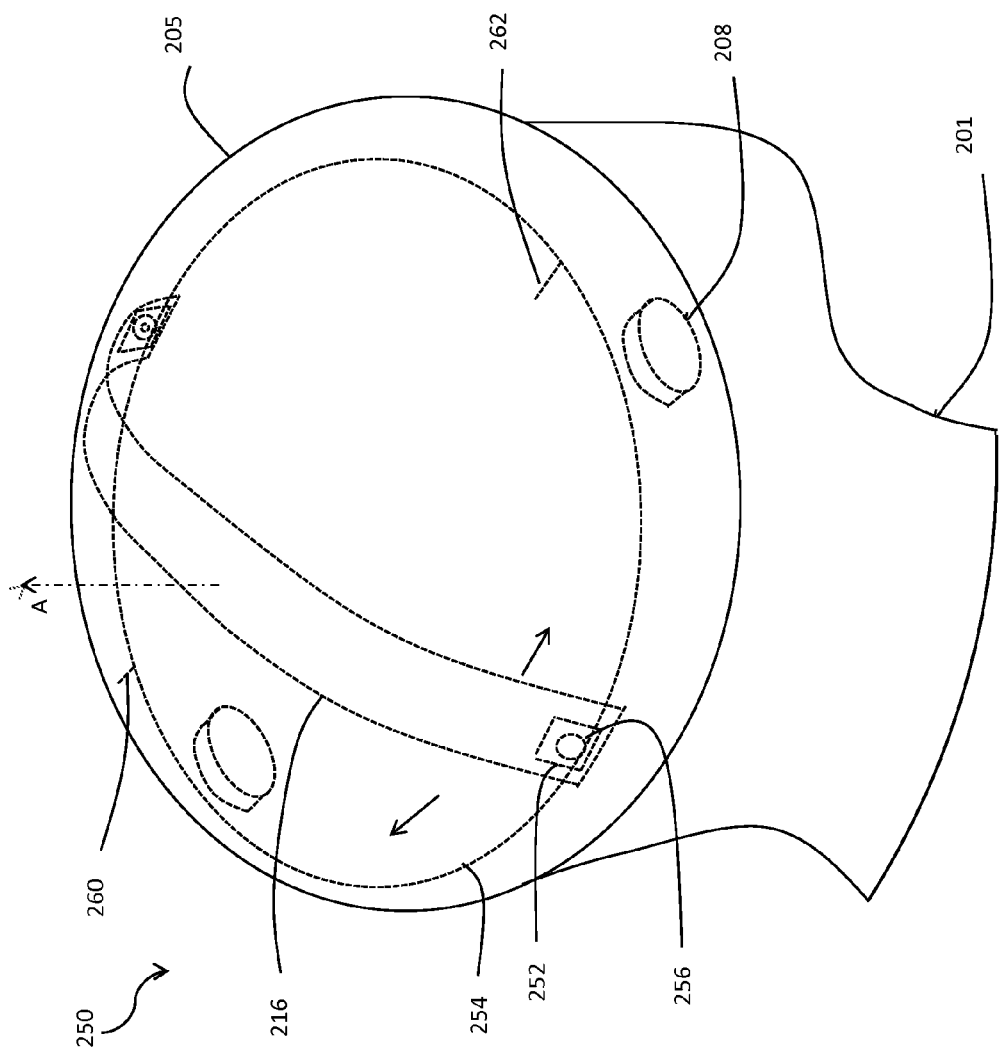
FIG. 13 is a perspective view of an example embodiment of a laser therapy helmet with a guide wire.

Reference is now made to FIG. 13, which illustrates an example of another embodiment of a laser therapy helmet device 250 that has a guide wire 254 which is used to rotate the emitter array housing 216 relative to the mount 205. In the illustrated embodiment, the helmet device 250 comprises a guide wire 254, an actuator 252, a guide wheel 256 and tie downs 260, 262. In the illustrated embodiment, the actuator 252 is coupled to the housing 216. The guide wheel 256 is rotationally coupled to the actuator 252 and is also rotationally coupled to the guide wire 254. The guide wire 254 is coupled to the mount 205 by the tie downs 260, 262 which prevent the guide wire 254 from moving relative to the mount 205 by more than a nominal distance. In use, when the actuator 252 rotates the guide wheel 256, the guide wheel 256 rotates relative to the guide wire 254, causing the emitter array housing 216 to rotate relative to the mount 205 and the user's head 201.

In some embodiments, the emitter array housing 216 comprises a biasing means (not shown) for biasing the guide wire 254 against the guide wheel 256, such that there is sufficient friction between the guide wheel 256 and the guide wire 254 so that when the guide wheel is rotated, the emitter array housing 216 rotates relative to the mount 205. In some embodiments, the biasing means comprises a spring-biased member extending from the emitter array housing 216 and providing a biasing force to rotatably couple the guide wheel 256 to the guide wire 254.

In some alternative embodiments, other elements may be used to prevent motion of the guide wire 254 with respect to the mount 205. For example, in some alternative embodiments, the guide wire 254 may be mounted within a groove (not shown) in the mount 205, wherein the groove is shaped to receive the guide wheel 256 and to encourage smooth rotation of the emitter array housing 216 about the mount 205.

In some alternative embodiments, the guide wire 254 may be circumferentially looped around the guide wheel 256.

In some alternative embodiments, the guide wire 254 may be coupled to the housing 216, while the actuator 252 and the guide wheel 256 may be coupled to the mount 205. In such embodiments, the guide wire 254 may be rigid and may not be circumferentially looped around the guide wheel 256.

In some alternative embodiments, the guide wheel 256 may be rotationally coupled to the guide wire 254 with a plurality of teeth and grooves.

In some alternative embodiments, the guide wheel 256 may comprise guide wheel teeth (not shown) and the guide wire 254 may comprise a plurality of guide wire grooves (not shown) for receiving the guide wheel teeth.

Reference is now made to FIG. 14 which illustrates an example of another embodiment of a laser therapy helmet device 270 that is ground-coupled. The helmet device 270 comprises a mount coupling structure 271, an actuator 272 and an emitter array housing 216. The mount 275 may directly or indirectly rest on a ground or another load-bearing surface, such that the weight of the helmet device 275 is substantially supported by the mount 275 instead of by the user's head 201. However, it is not necessary that the mount 275 be rigidly coupled to the ground. For example, mount 275 may be a sliding mount or a rolling mount.

In some alternative embodiments, the actuator 272 may be rigidly coupled to the mount coupling structure 271 and rotationally coupled to the emitter array housing 216, such that in use, the actuator 272 rotates the emitter array housing 216 about the mount 275 and the user's head 201.

In some alternative embodiments, the actuator 272 may be rigidly coupled to the emitter array housing 216 and rotationally coupled to the mount coupling structure 271.

In some alternative embodiments, the actuator 272 may be rigidly coupled to the mount 275 and rotationally coupled to the mount coupling structure 271, such that in use, the actuator 272 rotates the mount coupling structure 271 about the mount 275.

In some alternative embodiments, the actuator 272 may be mounted to the mount 275 and force from the actuator 272 may be translated through the mount coupling structure 271 to the emitter array housing 216 through a translation element such as, but not limited to, a belt system, for example.

Reference is now made to FIGS. 15A and 15B, which illustrate examples of alternative embodiments of emitter array housings for use with laser therapy helmet devices. In the illustrated embodiments, the emitters 102 are mounted to the emitter array housings 286 and 296 such that when activated the emitters 102 emit coherent light away from the active surfaces 288 and 298, respectively, towards the user's treatment surface (when in use). In FIG. 15A, the emitter array housing 286 is shaped as a cross. In FIG. 15B, the emitter array housing 296 includes an emitter array active surface 298 having a plurality of parallel emitter active surfaces. Although the emitter array active surface 298 illustrates three active surfaces, there may be embodiments with more active surfaces.

Figure 16:
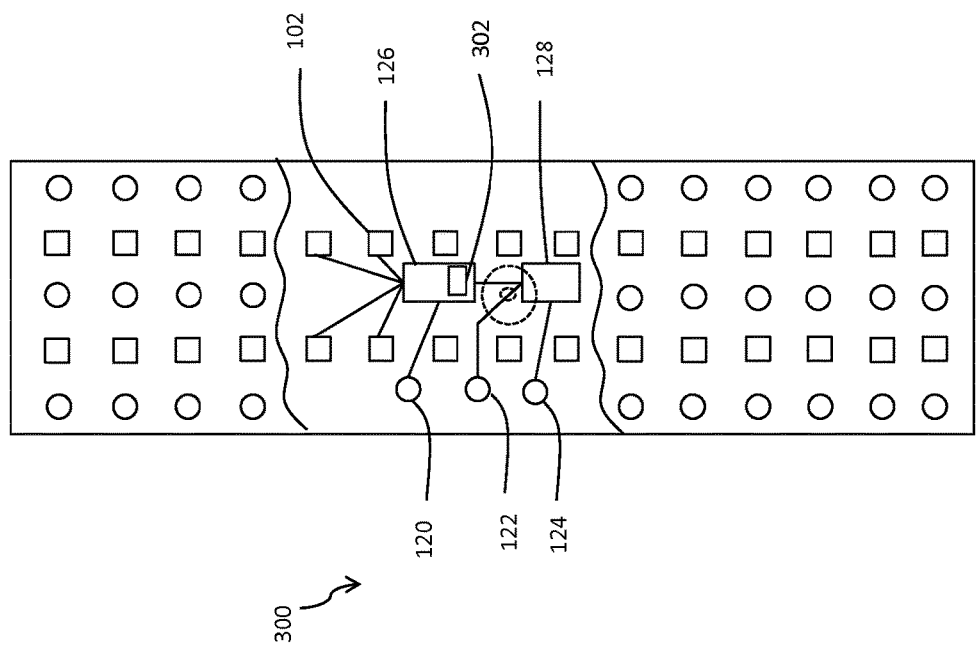
FIG. 16 is a cutaway bottom view of a laser therapy helmet module.

Reference is now made to FIGS. 16-17, which illustrate a laser therapy module 300 that may be used with the various helmet devices shown herein. The laser therapy module 300 comprises emitters 102; a variable control module 126 coupled to the emitters 102 for controlling the emitters 102, and a power module 128 coupled to the variable control module 126 for powering the emitters 102. The laser therapy module 300 is generally mounted in the emitter array housing 216. The laser therapy module 300 further comprises at least one of a user interface 120, a power switch 122, and a power indicator 124. The laser therapy module 300 is thus similar to the laser therapy module 121, which is described in relation to FIG. 4, in that the elements that are in common for both the laser therapy module 121 and the laser therapy module 300 operate in a similar manner. The laser therapy module 300 further comprises an actuator control module 302 for controlling the actuator 202. The actuator 202 is generally powered by the power module 128. Each of these components may be mounted on one or more circuit boards as was similarly described for the brush device 100.

The actuator control module 302 can selectively activate, deactivate, or otherwise control actuator 202. In some embodiments, the actuator control module 302 is operable to vary the output of actuator 202, such that in use, the actuator control module 302 can vary the rotational speed and acceleration between the emitter array housing 216 and the mount 205. The actuator control module 302 may comprise a processor, an ASIC, a hardware controller and the like, which can be programmed or otherwise configured to provide control signals. Accordingly, the actuator control module 302 may be provided with software instructions to implement certain functionality.

Further, in some embodiments, the actuator control module 302 may be operable to control the output of the actuator 202 depending on the mode of operation of the device, as selected at the user interface 120.

Additionally, in some embodiments, the user can interface with the user interface 120 to control the actuator 202. For example, in some embodiments, the user may be able to use the user interface 120 to modify the force exerted by the actuator 202 (and thus the rotational speed of the housing 216) in the modes of operation by providing an appropriate input to the actuator control module 302.

Although, the laser therapy module 300 was described in relation to the helmet device 200, the elements of the laser therapy module 300 may be varied in position or structure to operate with the actuators 232, 252 or 272, or the mount 275 of the helmet devices 230, 250 and 270. For example, FIG. 17 illustrates an example embodiment in which the laser therapy module 300 is mounted within the mount 205 instead of within the emitter array housing 216.

Reference is now made to FIGS. 18A-18C, which illustrate an example for several steps of a sequential activation mode of operation of the laser therapy helmet device 200, in which at least one band of light propagates across the rows of laser emitters by activating certain rows of emitters in successive steps. As with the brush device 100 described in relation to FIGS. 6A-6C, sequential activation mode of operation of the helmet device 200 is best suited for thin-haired individuals to prevent overstimulation. In this example sequential mode of operation, the helmet device 200 comprises a group of activated laser emitters 310 and a group of deactivated laser emitters 312. The implementation of the sequential mode of operation illustrated in FIGS. 18A-18C is somewhat similar to the implementation of the sequential mode of operation described in relation to FIGS. 6A-6C. In the sequential mode of operation illustrated in FIGS. 18A-18C two bands of light may be generated by separating two activated emitters groups 316 and 318 by a group of inactive emitters. While, the sequential mode of operation shown in FIGS. 18A-18C is described in relation to the helmet device 200, the pattern in this mode of operation may also be used with one of the brush devices described herein. However, the higher number of emitters 102 on the helmet device 200 may facilitate different patterns of sequential activation that are not possible with a brush device. For example, the thickness of the light bands may be smaller for a brush device compared to a helmet device. Also, for the helmet device, the sequential mode of operation may use a less than three or more than three rows of active emitters for the light bands. The helmet devices 230, 250 or 270 may also comprise a sequential mode of operation.

Reference is now made to FIGS. 19A-19B, which illustrate an example of a mode of operation of the laser therapy brush device 100 and the laser therapy helmet device 200 in which a combination of continuous emitters and pulsing emitters are active. This therapy mode is best suited for individuals with moderate hair loss to create effective biostimulation while simultaneously decreasing the possibility of overstimulation. In the laser therapy brush device 100 and the laser therapy helmet device 200, the variable control module 126 controls the emitters 102 such that a plurality of the emitters 102 operate as continuous emitters 320 and at least one emitter 102 operates as a pulsing emitter 322. A continuous emitter is an emitter that is continuously powered, such that it continuously emits coherent light. A pulsing emitter is an emitter that rapidly switches (or is switched) from outputting coherent light to not outputting coherent light, which reduces the average output power from the laser emitter to the user's treatment surface. In the illustrated embodiments, pulsing may be achieved by rapidly switching laser emitters on and off.

There may be other embodiments that provide pulsing laser light emission from laser light emitters. For example, in some alternative embodiments, continuous laser emitters and an optical modulator may be used, such that the optical modulator is operated to only let light pass through for successive short periods of time during operation. In other alternative embodiments, at least one of Q switching, mode locking, cavity dumping, gain switching, and/or opto-electronic oscillators, for example, may be used to provide pulsing laser light emission.

It some embodiments, the helmet devices 230, 250 or 270 may also comprise a mode of operation in which one or more combinations of continuous and pulsing emitters are active.

Reference is now made to FIG. 20, which shows a block diagram of an example embodiment of a laser emitter module which may be used with any of the various embodiments of the laser therapy brush device or the laser therapy helmet device described herein to selectively activate emitters 102 in order to carry out one of the modes of operation. The majority of these components have been described previously.

The control module 126 comprises a control unit 402 and a switching network 404. Each of the laser emitters 102 may be directly coupled to the switching network 404 which is in turn coupled to the control unit 402. The control unit 402 may be implemented as a processor, an ASIC, a hardware controller and the like, which can be programmed or otherwise configured to provide control signals. Accordingly, the control unit 402 may be provided with software instructions to implement certain functionality depending on its implementation.

In this example embodiment, each of the emitters 102 may be independently wired to the switching network 404 to allow the control unit 402 to send control signals individually to the emitters 102 to have them operate according to a selected mode of operation. The switching network may be implemented using NMOS or CMOS transistors that operate as switches or using other components that are suitable to operate as switches such as diodes, for example.

The control unit 402 controls the operation of the various brush devices and helmet devices described herein. The control unit 402 provides control signals to the switching network 404 to activate or deactivate the emitters 102 according to a desired sequence or mode of operation. The user interface 120 allows a user to select the mode of operation, or in some embodiments to customize the operation of the brush devices or the helmet devices described herein.

For the various helmet devices described herein, the block diagram of FIG. 20 may be modified by adding a connection between the control unit 402 and the actuators 202, 232, 252 and 272 (depending on the embodiment). Furthermore, in each of these cases, the actuator control module 302 may be implemented by the control unit 402.

Reference is now made to FIG. 21, which shows a block diagram of the laser emitter module when the laser emitters 102 are configured as groups of pulsed emitters 322 and continuous emitters 324. In this case, the control signals are provided from the control unit 402 and the switching network 404 so that it appears as if the emitters in the sets of pulsed emitters 322 are connected in parallel and the emitters in the set of continuous emitters 324 are connected in parallel. The control unit 402 may send control signals to the switching network 404 to activate or deactivate the sets of emitters 322 and 324, in conjunction with a timer. In other embodiments, other wiring or switches may be used to generate different activation patterns.

Reference is now made to FIG. 22, which shows a block diagram of the laser emitter module of FIG. 20 when the laser emitters 102 are grouped in rows for sequential activation. In this case, the control signals may be provided from the control unit 402 and the switching network 404 so that it appears as if the emitters in each row are connected in in parallel with one another but connected independently of the emitters in the other rows/columns. The control unit 402 and the switching network 404 operate to activate or deactivate the rows or columns of emitters 102, optionally in conjunction with a timer.

The laser emitter module of any of the various embodiments described in accordance with the teachings herein may be configured such that all of the modes of operation are user-selectable on a single device. Accordingly, the laser emitter module may be configured such that the switch network is operable to send control signals to groups of emitters for sequential activation as in FIG. 21, and separately to pulsing and continuous emitters as in FIG. 22. Additionally, or alternatively, the laser emitter module may be operable to send control signals to individual emitters.

The various embodiments of the apparatuses described in accordance with the teachings herein may be used to implement a method of treating hair loss. Using a laser brush device or a laser helmet device, as taught herein, to treat hair loss may comprise at least the steps of: assessing the user's current hair loss; selecting one or more modes of operation based on the user's current hair loss to deliver an optimum amount of light energy to the treatment surface such that the use is tailored to the user's amount of hair loss; activating the device according to one of the one or more modes of operation and bringing it into contact or close proximity with the treatment surface such that the treatment surface receives coherent light from laser emitters provided on the device; and, either moving an active surface of the device across the treatment surface or keep the active surface stationary if the activation pattern is stationary or non-stationary, respectively, while the device is activated.

In some embodiments, it may be beneficial to use more than one mode of operation with the same user where different modes of operation may be used in different treatment sessions, for example.

In some alternate uses, during a single treatment session, a user may select a first mode of operation and later may select a second mode of operation part-way through the treatment session, such that the treatment session comprises a combination of modes of operation to provide an optimum amount of laser energy to the user treatment surface.

Various embodiments of apparatus and devices have been described herein by way of example only. Furthermore, the apparatus and methods described herein may be used for the treatment of conditions other than alopecia, such as to treat scalp wounds, diabetic ulcers, and/or other ulcers to improve healing time. Various modifications and variations may be made to these example embodiments without departing from the spirit and scope of the embodiments, which is limited only by the appended claims which should be given the broadest interpretation consistent with the description as a whole.

REFERENCES

Budd, D., Himmelberger, D., Rhodes, T., Cash, T. E., Girman, C. J., *The effects of hair loss in European men: a survey in four countries*, European Journal of Dermatology. Volume 10, Number 2, 122-7, March 2000, Cas cliniques, http://www.jle.com/e-docs/00/01/89/92/article.phtml Leavitt, Matt L. Follicle facts. In: Haber R S, Stough D B (eds) Hair transplantation. Elsevier Saunders, Philadelphia, 2006. p 189

Unger, Martin G., Low-Level Laser Therapy Is Now A Do-It-Yourself Treatment, press release of the International Society Of Hair Restoration Surgery, New York, Oct. 16, 2003. http://www.ishrs.org/press-release/low-level-laser-therapy-now-do-it-yourself-treatment.

We claim:

1. A laser therapy device comprising:
an emitter array housing having an active surface with at least one concave shape, the active surface being adapted to face a treatment surface of a user for treating hair loss during use;
a plurality of bristles mounted to the emitter array housing and extending outwardly from the active surface;
a light therapy module positioned at least partially within the emitter array housing, the light therapy module having:
a plurality of emitters for emitting coherent light away from the active surface at a wavelength suitable for treating hair loss;
a variable control module coupled to the emitters for controlling the emitters; and a power module coupled to the variable control module for powering the emitters, a rotational coupling coupled to the emitter array housing;

a mount configured to receive a portion of the rotational coupling;

an actuator coupled to the rotational coupling and configured to rotate the emitter array housing with respect to the mount during use, wherein the bristles and the emitters are arranged in a plurality of rows and in each row the emitters and bristles are arranged substantially linearly;

wherein the device comprises a plurality of modes of operation for delivering varying amounts of light energy to the treatment surface of the user, wherein a mode of operation is chosen based on an amount of hair loss experienced by the user to more effectively tailor the treatment to the user's amount of hair loss; and wherein the device is shaped as a helmet.

2. The device of claim 1, wherein at least one of the rows comprise at least one emitter and at least two bristles arranged on either side of the at least one emitter.

3. The device of claim 1, wherein in a first mode of operation, at least one of the plurality of emitters is controlled to emit coherent light continuously, and at least a second one of the plurality of emitters is controlled to emit coherent light in a pulsed fashion.

4. The device of claim 1, wherein in a second mode of operation the variable control module is configured to sequence the emitters, wherein sequencing the emitters comprises sequentially activating and deactivating rows of emitters, such that at least one band of light energy is emitted along the rows of emitters.

5. The device of claim 4, wherein the sequencing comprises deactivating at least one row of emitters and activating at least one adjacent row of emitters.

6. The device of claim 4, wherein the at least one band of light energy is emitted along a plurality of adjacent rows of the emitters, and wherein the sequencing comprises deactivating at least one of the plurality of adjacent rows of emitters and activating at least one row of emitters adjacent to the plurality of rows of activated emitters.

7. The device of claim 4, wherein operating the emitters according to a second sequence comprises activating rows of emitters that are not adjacent to one another.

8. The device of claim 4, wherein the plurality of emitters are sequenced to move at least one light band relative to the active surface during use by activating and deactivating at least one of the plurality of rows of emitters along a common direction wherein the rows of activated emitters are adjacent to one another or are separated by at least one row of deactivated emitters.

9. The device of claim 1, wherein in a third mode of operation, every emitter in the plurality of emitters is controlled to emit coherent light continuously.

10. The device of claim 1, further comprising a user interface to allow a user to select between the modes of operation.

11. The device of claim 1, wherein the variable control module further comprises:

a control unit for generating control signals; and a switching network coupled between the plurality of emitters and the control unit for receiving the control signals in order to switch at least one emitter between an active state and an inactive state during use according to the mode of operation.

12. The device of claim 1, wherein the device is shaped as a brush.

13. The device of claim 1, wherein the actuator is rigidly coupled to the mount or to the emitter array housing.

14. The device of claim 1, wherein the mount comprises a spacer for resting the device on a portion of the user, such that the active surface is in a spaced relationship with the treatment surface.

15. The device of claim 1, wherein the mount comprises a circumferential guide track and the emitter array housing comprises a guide in mating relationship with the guide track, and wherein in use the actuator displaces the guide to rotate the emitter array housing relative to the mount.

16. The device of claim 1, wherein the mount rests on a support, such that the mount supports the weight of the device.

* * * * *